United States Patent [19]
Johnson et al.

[11] Patent Number: 5,874,298
[45] Date of Patent: Feb. 23, 1999

[54] **INSECTICIDAL TOXINS FROM *BRACON HEBETOR* NUCLEIC ACID ENCODING SAID TOXIN AND METHODS OF USE**

[75] Inventors: Janice H. Johnson; Robert M. Kral, Jr.; Karen Krapcho, all of Salt Lake City, Utah

[73] Assignee: NPS Pharmaceuticals, Inc., Salt Lake City, Utah

[21] Appl. No.: 392,546

[22] Filed: Feb. 17, 1995

[51] Int. Cl.$^6$ .............................. C12N 5/00; C12N 15/00; C07H 17/00; C07K 14/00
[52] U.S. Cl. .................. 435/325; 435/320.1; 435/69.1; 536/23.1; 514/12; 530/350
[58] Field of Search .............................. 574/12; 530/350; 435/69.1, 325, 320.1; 536/23.1

[56] References Cited

U.S. PATENT DOCUMENTS

| | | | |
|---|---|---|---|
| 4,925,664 | 5/1990 | Jackson et al. | 424/537 |
| 5,037,846 | 8/1991 | Saccomano et al. | 514/419 |
| 5,185,369 | 2/1993 | Saccomano et al. | 514/502 |
| 5,227,397 | 7/1993 | Saccomano et al. | 514/419 |
| 5,554,592 | 9/1996 | Quistad et al. | 514/12 |

FOREIGN PATENT DOCUMENTS

| | | | |
|---|---|---|---|
| 2005658 | 6/1990 | Canada | C12N 15/12 |
| 9423540 | 11/1994 | United Kingdom . | |
| 9501074 | 1/1995 | United Kingdom . | |
| 9513293 | 6/1995 | United Kingdom . | |
| WO93/18145 | 9/1993 | WIPO | C12N 15/12 |
| WO96/16171 | 5/1996 | WIPO . | |

OTHER PUBLICATIONS

"Overproduction of Encapsulated Insecticidal Crystal Proteins in a *Bacillus thuringiensis spoOA* Mutant", Lereclus et al., *Bio/Technology*, vol. 13, Jan. 13, 1995, p. 67.

"Insecticidal Activity of Spider (Araneae), Centipede (Chilopoda), Scorpion (Scorpionida), and Snake (Serpentes) Venoms", Quistad et al., *Journal of Economic Entomology*, vol. 85, No. 1, Feb. 1992, pp. 33–39.

"Development of a Recombinant Baculovirus Expressing an Insect–Selective Neurotoxin: Potential for Pest Control", McCutchen et al., *Bio/Technology*, vol. 9, Sep. 1991, pp. 848–852.

"Identification of Insecticidal Peptides from Venom of the Trap–Door Spider, *Aptostichus Schlingeri* (Ctenizidae)", Skinner et al., *Toxicon*, vol. 30, No. 9, 1992, pp. 1043–1050.

"Neurotoxins from Venoms of the Hymenoptera–Twenty–Five Years of Research in Amsterdam", Tom Piek, *Comp. Biochem. Physiol.*, vol. 96C, No. 2, 1990, pp. 223–233.

"Curatoxins, Neurotoxic Insecticidal Polypeptides Isolated From the Funnel–Web Spider *Hololena Curta*", Stapleton et al., *The Journal of Biological Chemistry*, vol. 265, No. 4, Feb. 5, 1990, pp. 2054–2059.

"Perspectives in Biochemistry", Lila M. Gierasch, *American Chemical Society*, vol. 28, No. 3, Feb. 7, 1989, pp. 923–030.

"Purification and Characterization of Two Classes of Neurotoxins from the Funnel Web Spider, *Agelenopsis aperta*", Skinner et al., *The Journal of Biological Chemistry*, vol. 264, No. 4, Feb. 5, 1989, pp. 2150–2155.

"Trends in the Development of Baculovirus Expression Vectors", Luckow et al., *Bio/Technology*, vol. 6, Jan. 1988, pp. 47–55.

"The Action of a Toxin From the Venom of the Wasp Habrobracon Hebetor (SAY) on the Neuromuscular Transmission of Insects", Slavnova et al., Institute For Bioorganic Chemistry, Apr. 16, 1987, pp. 1–3.

Characterization of Two Paralysing Protein Toxins (A–MTX and B–MTX), Isolated from a Homogenate of the Wasp *Microbracon Hebetor* (SAY), Visser et al., *Comp. Biochem. Physiol.*, vol. 75B, No. 3, 1983, pp. 523–530.

Two Different Paralysing Preparations Obtained from a Homogenate of the Wasp *Microbracon Hebetor* (SAY), Spanjer et al., *Toxicon*, vol. 15, 1987 pp. 413–421.

Isolation and Some Biochemical Properties of a Paralysing Toxin from the Venom of the Wasp *Microbracon Hebetor* (SAY), Visser et al., *Toxicon*, vol. 14, 1976, pp. 357–370.

"Short Communication Stability of *Microbracon Hebetor* (SAY) Venom Preparations", D. Drenth, *Toxicon*, vol. 12, pp. 541–542.

*Primary Examiner*—Karen Cochrane-Carlson
*Attorney, Agent, or Firm*—Madson & Metcalf

[57] ABSTRACT

This invention relates to the purification of a group of insecticidally effective toxins isolated from the wasp, *Bracon hebetor*, characterized by their neurotoxic effect on insect pest and low mammalian toxicity. The cDNA sequences for two of these toxins have been isolated, and the complete coding sequence is provided. This invention also discloses methods for producing recombinant toxins, as well as methods of utilizing these toxins as insecticidal agents.

13 Claims, 3 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 142 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL:

( i v ) ANTI-SENSE: no ( v ) FRAGMENT TYPE:

( v i ) ORIGINAL SOURCE:
        ( A ) ORGANISM: Bracon hebetor
        ( C ) INDIVIDUAL ISOLATE: 16 kDa toxin ( x i ) SEQUENCE DESCRIPTION: SEQ ID NO:1:

```
Phe Asn Pro Glu Thr His Arg Glu Cys Lys Asn Tyr Cys Ala Lys
 1               5                  10                  15

Glu His Gly Glu Glu Tyr Arg Thr Trp Ser Phe Arg Tyr Glu Leu
                20                  25                  30

Gly Asp Ile Phe Lys Cys Val Cys Thr His Gly Lys Asn Leu Met
                35                  40                  45

Gly Ser Glu Asn Tyr Gly Lys Cys Arg Glu Ala Cys Ile Gln Asn
                50                  55                  60

His Gly Ala Gly Gly Phe Lys Tyr Ala Phe Pro Ile Tyr Ser Glu
                65                  70                  75

Val Pro Ala Ser Trp Ala Cys Ile Cys Thr Gln Glu Lys Asn Lys
                80                  85                  90

Thr Phe Cys Ile His Ala Cys Ser Glu Ile His His Lys Ala Pro
                95                  100                 105

Pro Lys Asn Pro Ile Val Met Lys Asn Gly Gln Cys Tyr Tyr Gln
                110                 115                 120

Asp His Arg Gly Val Asp Arg Tyr Cys Glu Val Tyr Met Lys Phe
                125                 130                 135

Lys Asp Ala Lys Glu Ser Ile
                140
```

( 2 ) INFORMATION FOR SEQ ID NO:2:

( i ) SEQUENCE CHARACTERISTICS:
        ( A ) LENGTH: 253 amino acids
        ( B ) TYPE: amino acids
        ( C ) STRANDEDNESS: single
        ( D ) TOPOLOGY: unknown ( i i ) MOLECULE TYPE: protein (iii) HYPOTHETICAL:

(iv) ANTI-SENSE: no (v) FRAGMENT TYPE:

(vi) ORIGINAL SOURCE:
(A) ORGANISM: Bracon hebetor
(C) INDIVIDUAL ISOLATE: 30 kDa toxin (xi) SEQUENCE DESCRIPTION: SEQ ID NO:2:

```
Ile Ile Asn Gly His Asp Ala Thr Glu Gly Gln Phe Pro His Met
1               5                   10                  15
Ala Tyr Leu Gln Ala Ser Ala Gly Lys Cys Ser Tyr Val Cys Gly
                20                  25                  30
Gly Ala Leu Leu Thr Lys Lys His Ile Met Thr Ala Ala His Cys
                35                  40                  45
Val Ala Met His Arg Thr Ala Asn Ile Lys Val Ala Leu Gly Val
                50                  55                  60
Thr Asp Phe His Asn Lys Pro Ser Met Gln Gln Arg Lys Val Glu
                65                  70                  75
His Ile Lys Val His Ser Glu Tyr Lys Gly Gly Arg Arg Lys Ser
                80                  85                  90
Leu Lys Asn Trp Tyr Arg Ser Ile His Arg Thr Phe Thr Gly Pro
                95                  100                 105
Ser Gly Asp Lys Glu Tyr Asn Asp Ile Ala Ile Ile Thr Leu Ser
                110                 115                 120
Gln Glu Val Thr Leu Gly Pro Val Val Lys Thr Ile Asn Leu Pro
                125                 130                 135
Pro Lys Ser Tyr Arg Leu Pro Phe Asp Gln Asp Ala Arg Leu Ser
                140                 145                 150
Gly Phe Gly Arg Thr Val Ile Val Lys Glu Asn Asp Pro Ile Pro
                155                 160                 165
Pro Pro Thr Thr His Leu Gln Trp Leu Asp Met Lys Val Leu His
                170                 175                 180
Ser Arg Asp Ala Ile Val Thr Asp Ser Glu Phe Leu Ala Asp Lys
                185                 190                 195
Glu Tyr Gly Asp Gly Thr Trp Ser Asn Ala Ala Lys Gly Asp Ser
                200                 205                 210
Gly Ser Pro Leu Val Lys Asp Asn Gln Val Ile Gly Val Ala Val
                215                 220                 225
Ser Val Ser Asp Glu Glu His Thr Thr Arg Phe Gln Ile Val Thr
                230                 235                 240
Tyr Tyr Leu Asp Trp Ile Lys Lys Tyr Ala Glu Leu Ala
                245                 250
```

(2) INFORMATION FOR SEQ ID NO:3:

(i) SEQUENCE CHARACTERISTICS:
(A) LENGTH: 617 nucleotides
(B) TYPE: nucleic acid
(C) STRANDEDNESS: double
(D) TOPOLOGY: unknown (ii) MOLECULE TYPE: cDNA (iii) HYPOTHETICAL:

(iv) ANTI-SENSE: yes (v) FRAGMENT TYPE:

(v i) ORIGINAL SOURCE:
(A) ORGANISM: Bracon hebetor
(C) INDIVIDUAL ISOLATE: 16 kDa toxin cDNA (x i) SEQUENCE DESCRIPTION: SEQ ID NO:3:

| GGCAC GAGTACAGTT TGGATAAATC | ATG Met -15 | AAA Lys | TTT Phe | TTA Leu | TAT Tyr | CTA Leu | ATA Ile -10 | CTC Leu | 49 |

| CTT Leu | TTA Leu | ATT Ile | GCA Ala -5 | GGA Gly | GTA Val | GCA Ala | TCA Ser | TTC Phe 1 | AAT Asn | CCG Pro | GAG Glu | ACA Thr | CAT His 5 | CGT Arg | 94 |

| GAA Glu | TGT Cys | AAG Lys 10 | AAT Asn | TAT Tyr | TGC Cys | GCC Ala | AAA Lys 15 | GAG Glu | CAC His | GGC Gly | GAG Glu | GAA Glu 20 | TAT Tyr | CGT Arg | 139 |

| ACG Thr | TGG Trp | TCT Ser 25 | TTC Phe | CGT Arg | TAC Tyr | GAA Glu | CTT Leu 30 | GGT Gly | GAT Asp | ATT Ile | TTT Phe | AAA Lys 35 | TGT Cys | GTT Val | 184 |

| TGC Cys | ACT Thr | CAC His 40 | GGA Gly | AAG Lys | AAT Asn | CTT Leu | ATG Met 45 | GGA Gly | AGC Ser | GAG Glu | AAT Asn | TAT Tyr 50 | GGT Gly | AAG Lys | 229 |

| TGT Cys | AGA Arg | GAA Glu 55 | GCA Ala | TGT Cys | ATT Ile | CAA Gln | AAT Asn 60 | CAT His | GGA Gly | GCG Ala | GGA Gly | GGC Gly 65 | TTT Phe | AAA Lys | 274 |

| TAT Tyr | GCC Ala | TTT Phe 70 | CCC Pro | ATA Ile | TAC Tyr | AGC Ser | GAA Glu 75 | GTA Val | CCA Pro | GCA Ala | TCA Ser | TGG Trp 80 | GCA Ala | TGC Cys | 319 |

| ATA Ile | TCG Cys | ACT Thr 85 | CAG Gln | GAG Glu | AAA Lys | AAT Asn | AAG Lys 90 | ACA Thr | TTT Phe | TGT Cys | ATA Ile | CAT His 95 | GCT Ala | TGC Cys | 364 |

| TCA Ser | GAA Glu | ATT Ile 100 | CAT His | CAC His | AAG Lys | GCC Ala | CCA Pro 105 | CCT Pro | AAG Lys | AAT Asn | CCC Pro | ATA Ile 110 | GTT Val | ATG Met | 409 |

| AAA Lys | AAT Asn | GGA Gly 115 | CAA Gln | TGC Cys | TAC Tyr | TAC Tyr | CAA Gln 120 | GAT Asp | CAC His | AGG Arg | GGT Gly | GTT Val 125 | GAC Asp | AGG Arg | 454 |

| TAT Tyr | TGT Cys | GAA Glu 130 | GTT Val | TAT Tyr | ATG Met | AAG Lys | TTC Phe 135 | TTA Leu | GAT Asp | GCG Ala | TTG Leu | GAA Glu 140 | TCA Ser | ATT Ile | 499 |

| TAACAATGAT CAAATTCATG TTATCAATGA AGGAAGAATA ATGAATCAAT | 549 |

| AATAATAATC AAAAATCAAT GATTTGTTT TTAATTATTA AAAAAAAAG | 599 |

| GCTACAAAAA CTCGTGCC | 617 |

(2) INFORMATION FOR SEQ ID NO:4:

(i) SEQUENCE CHARACTERISTICS:
(A) LENGTH: 1127 nucleic acid
(B) TYPE: nucleic acid
(C) STRANDEDNESS: double
(D) TOPOLOGY: unknown (i i) MOLECULE TYPE: cDNA (i i i) HYPOTHETICAL:

(i v) ANTI-SENSE: yes (v) FRAGMENT TYPE:

(v i) ORIGINAL SOURCE:
(A) ORGANISM: Bracon hebetor
(C) INDIVIDUAL ISOLATE: 30 kDa toxin cDNA (x i) SEQUENCE DESCRIPTION: SEQ ID NO:4:

| GGC ACGAGTGGCA | 13 |

```
TTGTTGATAT ATAACAATTT ATTAAAAATT TCAAGTGGAA AGAAAAACTA                                              63

TCTTGTTTTT TTTTTTGTTT TTTTTCATAA TTTAAA ATG CAT TTC TTC GCC                                        114
                                         Met His Phe Phe Ala
                                             -20

TCC ATC CTG GTA TGC TTC TTA CTG GGC AAG GCA ATT CAT GAT GTG                                        159
Ser Ile Leu Val Cys Phe Leu Leu Gly Lys Ala Ile His Asp Val
        -15              -10                         -5

GAA GGA ATA ATA AAT GGT CAT GAT GCT ACT GAG GGA CAA TTT CCC                                        204
Glu Gly Ile Ile Asn Gly His Asp Ala Thr Glu Gly Gln Phe Pro
         1               5                    10

CAT ATG GCT TAT TTA CAA GCA TCA GCT GGA AAG TGT TCT TAT GTA                                        249
His Met Ala Tyr Leu Gln Ala Ser Ala Gly Lys Cys Ser Tyr Val
     15              20                  25

TGT GGC GGT GCT CTT CTA ACT AAA AAA CAT ATT ATG ACA GCT GCT                                        294
Cys Gly Gly Ala Leu Leu Thr Lys Lys His Ile Met Thr Ala Ala
     30              35                  40

CAT TGT GTA GCA ATG CAC AGA ACG GCA AAT ATT AAA GTA GCC CTT                                        339
His Cys Val Ala Met His Arg Thr Ala Asn Ile Lys Val Ala Leu
     45              50                  55

GGT GTT ACG GAT TTT CAT AAT AAG CCA TCA ATG CAA CAA AGA AAG                                        384
Gly Val Thr Asp Phe His Asn Lys Pro Ser Met Gln Gln Arg Lys
     60              65                  70

GTT GAA CAT ATA AAA GTC CAT TCT GAG TAC AAA GGA GGA AGG CGT                                        429
Val Glu His Ile Lys Val His Ser Glu Tyr Lys Gly Gly Arg Arg
     75              80                  85

AAG TCA TTA AAA AAT TGG TAT CGC TCC ATA CAT CGT ACA TTT ACA                                        474
Lys Ser Leu Lys Asn Trp Tyr Arg Ser Ile His Arg Thr Phe Thr
     90              95                 100

GGA CCG TCT GGG GAT AAA GAA TAC AAT GAT ATT GCT ATT ATA ACG                                        519
Gly Pro Ser Gly Asp Lys Glu Tyr Asn Asp Ile Ala Ile Ile Thr
    105             110                 115

TTG AGC CAG GAA GTA ACA CTA GGA CCA GTA GTA AAG ACT ATT AAT                                        564
Leu Ser Gln Glu Val Thr Leu Gly Pro Val Val Lys Thr Ile Asn
    120             125                 130

TTA CCC CCA AAG AGC TAT CGG CTT CCT TTT GAT CAA GAT GCT AGA                                        609
Leu Pro Pro Lys Ser Tyr Arg Leu Pro Phe Asp Gln Asp Ala Arg
    135             140                 145

TTG TCG GGC TTT GGC CGA ACA GTC ATT GTC AAA GAA AAT GAT CCA                                        654
Leu Ser Gly Phe Gly Arg Thr Val Ile Val Lys Glu Asn Asp Pro
    150             155                 160

ATT CCT CCA CCC ACT ACA CAT TTA CAA TGG CTA GAT ATG AAG GTT                                        699
Ile Pro Pro Pro Thr Thr His Leu Gln Trp Leu Asp Met Lys Val
    165             170                 175

CTT CAT TCA CGA GAT GCT ATT GTC ACT GAT AGT GAA TTT CTC GCT                                        744
Leu His Ser Arg Asp Ala Ile Val Thr Asp Ser Glu Phe Leu Ala
    180             185                 190

GAT AAA GAA TAT GGT GAT GGA ACT TGG TCT AAT GCA GCT AAG GGA                                        789
Asp Lys Glu Tyr Gly Asp Gly Thr Trp Ser Asn Ala Ala Lys Gly
    195             200                 205

GAC AGC GGT AGT CCC TTA GTC AAG GAT AAT CAA GTA ATT GGC GTA                                        834
Asp Ser Gly Ser Pro Leu Val Lys Asp Asn Gln Val Ile Gly Val
    210             215                 220

GCC GTT TCT GTG AGT GAT GAA GAA CAT ACT ACA GCG TTT CAA ATA                                        879
Ala Val Ser Val Ser Asp Glu Glu His Thr Thr Arg Phe Gln Ile
    225             230                 235

GTC ACT TAT TAT TTG GAT TGG ATC AAG AAA TAT GCC GAA CTT GCG                                        924
Val Thr Tyr Tyr Leu Asp Trp Ile Lys Lys Tyr Ala Glu Leu Ala
    240             245                 250

TAAAAAGAAT AAAGAGCAAA ATTGCTCAGA TGGTGAATAT ACATTTTTCC                                             974
```

```
AATAAGCTCA    TTTTTCTTAT    TTCTCGTTTT    AACGAGTCTA    CCACTTATAT              1024

GTAAAAAGGT    TATTCGAGAG    AAAAAATCGA    TTTATATGTA    ATTAAAAAAT              1074

TAAAGATTGT    TTTTTCTCTT    TTAACAGAAG    AAATTTGAAA    ATAAATTCTC              1124

GTG                                                                             1127
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: unknown (ii) MOLECULE TYPE: protein (iii) HYPOTHETICAL: no (iv) ANTI-SENSE: no (v) FRAGMENT TYPE: N-terminal fragment (vi) ORIGINAL SOURCE:
        (A) ORGANISM: Bracon hebetor
        (C) INDIVIDUAL ISOLATE: 16 kDa toxin NT (xi) SEQUENCE DESCRIPTION: SEQ ID NO:5:

```
Phe  Asn  Pro  Glu  Thr  His  Arg  Glu  Xaa  Lys  Asn  Tyr  Xaa  Ala  Lys
1                   5                        10                       15
Glu  His  Gly  Glu  Glu  Tyr  Arg
                    20
```

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: protein (iii) HYPOTHETICAL: no (iv) ANTI-SENSE: no (v) FRAGMENT TYPE: N-terminal fragment (vi) ORIGINAL SOURCE:
        (A) ORGANISM: Bracon hebetor
        (C) INDIVIDUAL ISOLATE: 30 kDa toxin NT (xi) SEQUENCE DESCRIPTION: SEQ ID NO:6:

```
Ile  Ile  Asn  Gly  His  Asp  Ala  Thr  Glu  Gly  Gln  Phe  Pro  His  Met
1                   5                        10                       15
Ala  Tyr  Leu  Gln  Ala  Ser  Ala  Gly
                    20
```

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: unknown (ii) MOLECULE TYPE: protein (iii) HYPOTHETICAL:

(i v) ANTI-SENSE: no (v) FRAGMENT TYPE: N-terminal fragment (v i) ORIGINAL SOURCE:
    (A) ORGANISM: Bracon hebetor
    (C) INDIVIDUAL ISOLATE: 18-1 toxin NT (i x) FEATURE:
    (A) NAME/KEY: Xaa
    (B) LOCATION: 4, 6, 8, 12, and 18
    (D) OTHER INFORMATION: Xaa at location 4 is either a leucine
        or glycine, Xaa a tyrosine or proline.

(x i) SEQUENCE DESCRIPTION: SEQ ID NO:7:

```
Thr Leu Phe Xaa Ala Pro Xaa Phe Xaa Gly
 1           5                    10
Arg Xaa Asp Lys Thr Phe Gly Xaa Gln Arg
                15              20
Phe Glu Gly Asp Val Gly
21              25
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: unknown (i i) MOLECULE TYPE: protein (i i i) HYPOTHETICAL:

(i v) ANTI-SENSE: no (v) FRAGMENT TYPE: N-terminal fragment (v i) ORIGINAL SOURCE:
        (A) ORGANISM: Bracon hebetor
        (C) INDIVIDUAL ISOLATE: 18-2 toxin NT (x i) SEQUENCE DESCRIPTION: SEQ ID NO:8:

```
Thr Leu Phe Thr Asp Arg Lys Trp Xaa Gly Arg Ala Asp Lys Thr
 1           5                    10                    15
Phe Gly Pro Ser Arg
                20
```

(2) INFORMATION FOR SEQ ID NO:9:

(i) SEQUENCE CHARACTERISTICS:
        (A) LENGTH: 23 nucleotides
        (B) TYPE: nucleic acid
        (C) STRANDEDNESS: single
        (D) TOPOLOGY: unknown (i i) MOLECULE TYPE: oligonucleotide (i i i) HYPOTHETICAL:

(i v) ANTI-SENSE: no (v i) ORIGINAL SOURCE:
        (A) ORGANISM: Bracon hebetor
        (C) INDIVIDUAL ISOLATE: 16 kDa degenerate oligo (i x) FEATURE:
        (A) NAME/KEY: N
        (B) LOCATION: 6
        (D) OTHER INFORMATION: N at position 6 is Y,N at position 12
          is R, and N at p (x i) SEQUENCE DESCRIPTION: SEQ ID NO:9:

```
TTCAANCCNG  ANACNCATNG  NGA                                                                              23
```

( 2 ) INFORMATION FOR SEQ ID NO:10:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: unknown ( i i ) MOLECULE TYPE: oligonucleotide ( i i i ) HYPOTHETICAL:

( i v ) ANTI-SENSE: no ( v i ) ORIGINAL SOURCE:
        ( A ) ORGANISM: Bracon hebetor
        ( C ) INDIVIDUAL ISOLATE: 30-1 kDa degenerate oligo ( i x ) FEATURE:
        ( A ) NAME/KEY: N
        ( B ) LOCATION: 3, 6, 15, and 18
        ( D ) OTHER INFORMATION: N at position 3, 6, 15, and 18 is Y.
        ( B ) LOCATION: 18
        ( D ) OTHER INFORMATION: The nucleotide is Y.

( x i ) SEQUENCE DESCRIPTION: SEQ ID NO:10:

```
ATNATNAACG  GNCANGANGC                                                                                   20
```

( 2 ) INFORMATION FOR SEQ ID NO:11:

( i ) SEQUENCE CHARACTERISTICS:
        ( A ) LENGTH: 29 nucleotides
        ( B ) TYPE: nucleic acid
        ( C ) STRANDEDNESS: single
        ( D ) TOPOLOGY: unknown ( i i ) MOLECULE TYPE: oligonucleotide ( i i i ) HYPOTHETICAL:

( i v ) ANTI-SENSE: no ( v i ) ORIGINAL SOURCE:
        ( A ) ORGANISM: Bracon hebetor
        ( C ) INDIVIDUAL ISOLATE: 30-2 kDa degenerate oligo ( i x ) FEATURE:
        ( A ) NAME/KEY: N
        ( B ) LOCATION: 3, 18, 21, and 23.
        ( D ) OTHER INFORMATION: N at position 3 and 18 is Y. N at
            position 21 is I, and N at positon 23 is M.

( x i ) SEQUENCE DESCRIPTION: SEQ ID NO:11:

```
GCNACNGAGG  GNCAGTTNCC  NCNNATGGC                                                                        29
```

INSECTICIDAL TOXINS FROM *BRACON HEBETOR* NUCLEIC ACID ENCODING SAID TOXIN AND METHODS OF USE

FIELD OF THE INVENTION

The present invention is related to toxins isolated from wasp venom which display insecticidal characteristics. More particularly, the present invention relates to insecticidally effective toxins isolated from the wasp *Bracon hebetor*, and other species of the genus Bracon, characterized by their neurotoxic effect on specific insect pests.

BACKGROUND OF THE INVENTION

Insects are among humankind's most serious competitors for food and fiber resources. Approximately one third of worldwide agricultural production is lost to insect damage each year. Insects such as termites and carpenter ants cause millions of dollars in structural damage every year. Many serious human and animal diseases, including malaria, yellow fever, sleeping sickness, viral encephalitis, and plague, are transmitted by insects. Efforts to control insect pests have resulted in the development of a global insecticide industry with annual sales of approximately $6 billion. Most of these products are synthetic chemical neurotoxins such as chlorinated hydrocarbons (e.g., DDT), carbamates (e.g., carbaryl), organophosphates (e.g., malathion), and synthetic pyrethroids (e.g., cypermethrin). Relatively minor, though significant, chemical insecticides include insect growth regulators (e.g., diflubenzuron and methoprene) and metabolic disrupters (e.g., hydroxymethylnon).

Synthetic chemical insecticides are effective for controlling pest insects in a wide variety of agricultural, urban, and public health situations. Unfortunately there are significant, often severe, side effects associated with the use of these products. Many pest populations have developed significant resistance to virtually all chemical insecticides, requiring higher and higher rates of usage for continued control. In a number of severe cases, highly resistant pest populations have developed which cannot be controlled by any available product. Chemical insecticides may also have deleterious effects on non-target organisms. Populations of beneficial arthropods, such as predators and parasites, are sometimes more severely affected by chemical applications than the pests themselves. Minor pests, ordinarily held in check by these beneficial organisms, may become serious pests when their natural constraints are removed by the use of chemical insecticides. Thus, new pest problems may be created by attempts to solve established problems.

Chemical insecticides may also have adverse effects on vertebrates. The use of DDT has been banned in the United States, due primarily to the insecticide's great environmental persistence and its resulting tendency to accumulate in the tissues of predatory birds, thereby disrupting their ability to produce viable eggs. The use of carbofuran has been severely restricted due to its avian toxicity, and many species of fish are known to be quite sensitive to a variety of insecticides. A number of insecticides, such as methyl parathion, are also quite toxic to humans and other mammals, and by accident or misuse have caused a number of human poisonings. Clearly, the field of insect control would benefit greatly from the discovery of insecticides with improved selectivity for insects and reduced effects on non-target organisms.

The problems described above, along with other concerns including the possibility that some insecticides may act as human carcinogens, have created a strong demand for the development of safer methods of insect control. The practice of integrated pest management (IPM), which seeks to minimize the adverse environmental effects of chemical insecticides by relying on cultural and biological methods, is one response to this demand. The success of IPM, however, has been less than hoped due to the lack of effective biological alternatives to chemical insecticides. Because these alternatives can reduce the frequency and severity of pest outbreaks and delay the development of insecticide-resistant pest populations, their availability is critical to the success of IPM programs.

Insect pathogens have been the objects of much study as potential pest control agents. Generally, these pathogens are quite selective for insects and in many cases affect only a few closely related species of insects. A number of insect pathogens have been developed as products, including bacteria (e.g., *Bacillus thuringiensis* and *Bacillus popiliae*), viruses (e.g., nuclear polyhedrosis viruses) and protozoa (e.g., the microsporidian Nosema locustae). These products occupy only a small fraction of the insecticide market, however, due largely to their relatively slow action. Although pathogens may ultimately cause a high level of mortality in pest populations, the insects may take weeks to die and continue to feed for much of that time. Thus, an unacceptably high level of crop or commodity damage may be inflicted before control is achieved. Currently, researchers are actively seeking ways to improve the effectiveness of insect pathogens and other biological control tools.

Insecticidal toxins from arthropods have been the objects of increasing interest over the past decade. These materials have proved useful for the detailed study of neural and neuromuscular physiology in insects. They have also been used to enhance the effectiveness of certain insect pathogens. The insecticidal toxin AaIT, from the scorpion *Androctonus australis*, has been employed for both purposes. This toxin belongs to a group of peptides that are lethal to a variety of insects but have no detectable effect in mammals, even though they come from a species known to be dangerous to humans. Other toxins in *A. australis* venom are lethal to mammals but have no effect on insects. This selectivity is particularly interesting in view of the fact that both groups of toxins act on voltage-sensitive sodium channels. Understanding the molecular basis of this selectivity may lead to the development of chemical insecticides with reduced effects on mammals and other non-target organisms.

The effectiveness of insect pathogens has also been enhanced by the use of genes encoding AaIT and other insect-selective toxins. A number of reports have demonstrated that the insecticidal properties of the *Autographa californica* nuclear polyhedrosis virus (AcMNPV), a member of the baculovirus family, can be enhanced by modifying the viral genome to include a gene encoding an insecticidal toxin. Toxins employed for this purpose include AaIT, TxP-1 from the parasitic mite *Pyemotes tritici*, DTX9.2 from the spider *Diguetia canities*, and NPS-326 (now known as TaITX-1) from the spider *Tegenaria agrestis*. These toxins were inserted into the AcMNPV genome under the control of either the p10 promoter or the polyhedrin promoter. Both promoters regulate the high-level expression of very late viral genes encoding component proteins of the viral occlusion bodies. In every case, recombinant viruses containing a toxin gene were more effective than the wild type virus, as measured by the time required for infected insects to die or become moribund.

Because the baculovirus system is well known to be a highly efficient and flexible method of expressing biologically active proteins from many different sources, it is reasonable to expect that newly discovered toxins will also be useful for enhancing the insecticidal activity of these viruses.

The use of these toxins is not expected to be limited to baculoviruses, however. Many other microbes, including bacteria and fungi, are known to be susceptible to such genetic manipulation. Certain bacteria and fungi, in fact, are widely used for large-scale production of exogenous proteins from humans and other mammalian sources; other insect viruses have also been studied as potential expression vectors. Examples of such pathogens include the entomopoxviruses, the bacterium *Escherischia coli*, and the fungus *Pichia pastoris*. Such pathogens may be enhanced as pest control agents by their modification to include toxin genes, much as the efficacy of baculoviruses has been enhanced by such modifications.

Thus it is clear that insecticidal toxins from arthropods may be used to advance the field of insect control in a number of significant ways. A novel composition of matter having the desired properties of insecticidal efficacy and insect selectivity, therefore, is expected to be useful in the art whether or not it can be used directly as an insecticidal compound. The means by which such a composition of matter may be made useful are well known to those skilled in the art, and are characterized by (but not limited to) the examples provided in the preceding paragraphs.

The venom of the wasp *Bracon hebetor* (also identified in the literature as *Microbracon hebetor* and *Habrobracon hebetor*) has been studied extensively due to its remarkable insecticidal potency. Thus, the present invention is directed to the isolation, purification, and identification of fractions of the venom of *Bracon hebetor*, and other species of the genus Bracon, which are useful in the study and control of insects.

SUMMARY OF THE INVENTION

The present invention relates to insecticidally effective toxins isolated from the wasp, *Bracon hebetor*, and other species of the genus Bracon such as *Bracon mellitor*, characterized by their neurotoxic effect on insect pests. These toxins are exemplified herein by the peptides SEQ ID NO:1 (also at times designated herein as "16 kDa toxin"), SEQ ID NO:2 (also at times designated herein as "30 kDa toxin"), two toxins at times designated the 18-1 toxin and the 18-2 toxin, and a fifth protein designated as the "20 kDa toxin," as well as the cDNA sequences of the 16 kDa and 30 kDa proteins designated SEQ ID NO:3 ("16 kDa toxin cDNA") and SEQ ID NO:4 ("30 kDa toxin cDNA"), respectively.

The characteristics of each of these toxins are more fully set forth below. However, when small quantities of a highly purified venom fraction containing these toxins are administered by injection into the abdomen of larvae of the tobacco budworm, the larvae are incapacitated by a flaccid paralysis. This highly purified fraction, and the methods for obtaining it, are also within the scope of this invention. Combinations of two or more of the toxins described above may be useful to obtain optimal insecticidal efficacy.

In another aspect, the present invention teaches methods for modifying and improving the described toxins for use as insecticidal agents. A signal sequence and propeptide sequence, for example, may be useful for efficiently secreting the wasp toxins or targeting them to a specific cell or location in a cell. Signal sequences may therefore obviate the need for lengthy purification procedures, as well as enhance the secretion and insecticidal efficacy of the wasp toxins.

Finally, the invention relates to the use of these toxins as agents for combating insect pests. Large quantities of these toxins may be obtained using known recombinant technology methods. The toxins can be engineered into an expression vector which is then inserted into either a prokaryotic host, such as *E. coli*, or a eukaryotic host, such as the insect cell line SF-9. The isolated protein may then be applied directly to the plant or animal sought to be protected from insect pests.

Alternatively, the toxins may be engineered into a natural pathogen of insects such as Bacillus or baculovirus. The recombinant pathogens can be utilized to transfer the peptides, or nucleic acids encoding the peptides, directly into the insect pests. These recombinantly engineered pathogens will have significantly increased insecticidal efficacy in comparison with the parental wild-type pathogens.

These and other objects and advantages of the invention will become apparent upon reading the following detailed description and appended claims, and upon reference to the accompanying drawings.

DETAILED DESCRIPTION OF THE DRAWINGS

Figure 5:
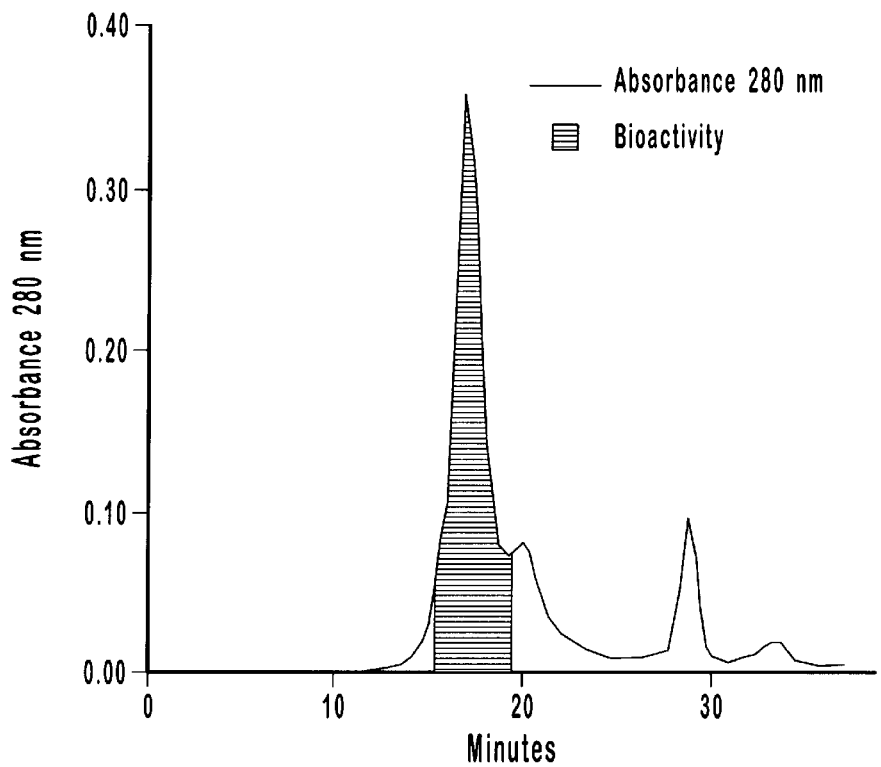
FIG. 5 is a chromatogram of the pooled active fractions from FIG. 4 subjected to anion-exchange chromatography on a Fractogel EMD TMAE-650 column and illustrates the biologically active pooled fractions eluted between 15–19.5 minutes.
Figure 6:
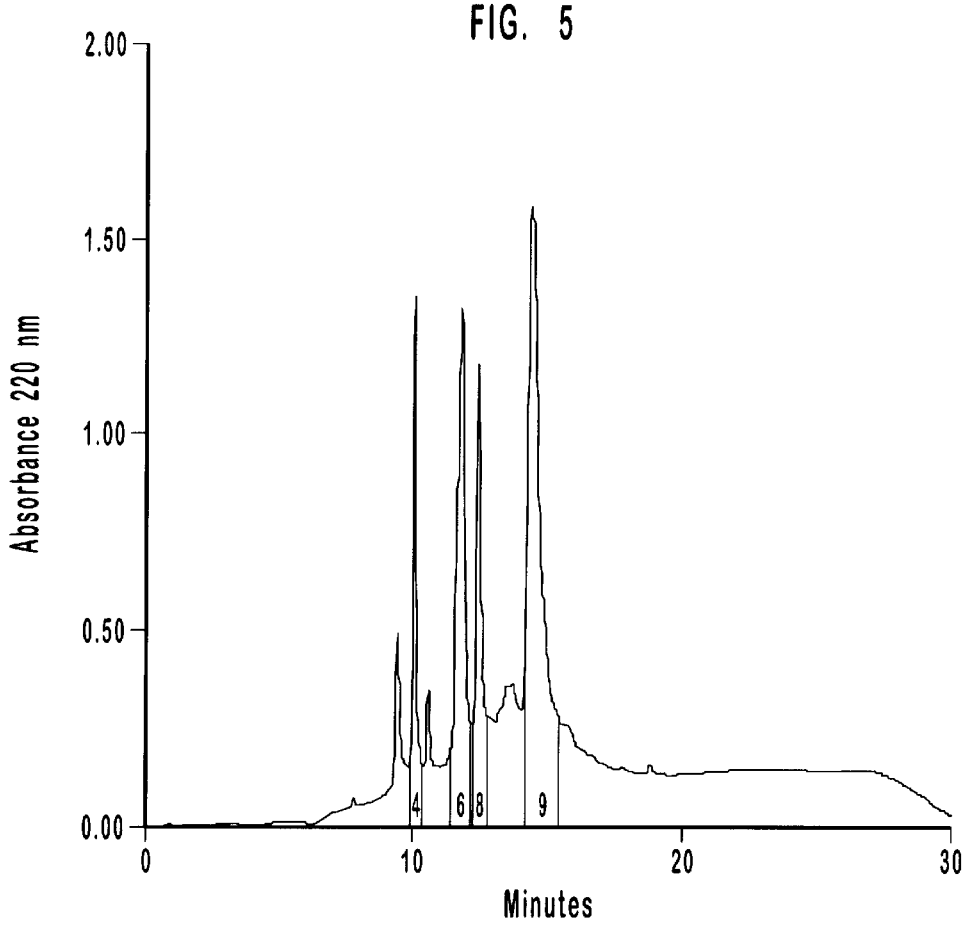

FIG. 6 is the chromatogram of the pooled active fractions from FIG. 5 subjected to reverse-phase chromatography on a Vydac C4 column. The four major peaks, corresponding to fractions 4, 6, 7 and 9, contain toxins SEQ ID NO:1, the 18-1 toxin, the 18-2 toxin, and SEQ ID NO:2, respectively. Fraction 9, in addition, contains a second component identified herein as the 20 kDa toxin.

DETAILED DESCRIPTION OF THE INVENTION

As discussed above, the present invention is related to toxins isolated from wasp venom which display insecticidal characteristics. More particularly, the present invention relates to a group of insecticidally effective toxins isolated wasps from the genus Bracon, characterized by their neurotoxic effect on selected insect pests. For the purposes of this application, the term "insecticidally effective" shall be defined as effective in incapacitating by flaccid paralysis the larvae of the tobacco budworm under the conditions set forth herein.

These toxins are exemplified herein by SEQ ID NO:1 (16 kDa toxin), SEQ ID NO:2 (30 kDa toxin), the 18-1 and 18-2 toxins, and the 20 kDa toxin, as well as the cDNA sequences for the 16 kDa and 30 kDa toxins designated SEQ ID NO:3 (16 kDa toxin cDNA), SEQ ID NO:4 (30 kDa toxin cDNA), respectively. Also described herein is a highly purified fraction containing these components and the methods for obtaining this fraction. Also set forth herein are methods for expression of these toxins by recombinant DNA methods. In addition, it is possible, by known techniques, to transform or transfect expression vectors containing a toxin cDNA sequence into a host cell or organism.

Accordingly, the present invention provides naturally occurring toxins for use as insecticides. The naturally occurring toxins may be used in a variety of ways to control insects, or to study the effects of such toxins on insects.

EXPERIMENTAL METHODS AND CHARACTERIZATION

The primary operative techniques and terms used in this specification are well known in the art. Nevertheless, in order to provide a clear understanding of the full scope of the present invention, reference is made to the following experimental methods and characterization techniques which may be used to practice the invention.

BIOLOGICAL ASSAYS

*Bracon hebetor* adults were laboratory-reared or obtained from commercial sources. *Bracon mellitor* adults were obtained from the USDA/ARS laboratory in Weslaco, Tex.

Assays for insecticidal activity were carried out in laboratory-reared, last instar larvae of the tobacco budworm, *Heliothis virescens* (TBW) or the beet armyworm, *Spodoptera exigua* (BAW). Extracts from whole wasps or dissected tissues (for the sake of brevity, these extracts are in some cases hereafter referred to as "venom") were characteristically prepared in phosphate-buffered physiological saline (PBS), pH 6.5, a second phosphate-buffered saline, pH 8.0, or a borate buffer, pH 9.0, which had been sterilized by membrane microfiltration (average pore width 0.2 micron).

All tissue homogenization, centrifugation, and filtration steps prior to the initiation of chromatography were carried out on ice or at a constant temperature of 4° C. Venom fractions were characteristically administered in the buffers used for the chromatographic separation; in most cases, tissue extracts were prepared in these chromatography buffers rather than in PBS. In every case, control larvae were treated with equivalent volumes of the appropriate buffer(s). All samples were administered by injection into the hemocoel of the larvae. The injection site was along the lateral midline between the third and seventh abdominal segments. After injection, larvae were held in individual Petri dishes with food and were observed periodically under a dissecting microscope. Larvae which could not right themselves within thirty seconds of being placed on their backs or sides were rated as paralyzed. Larvae which displayed a significantly compromised righting response (between ten and thirty seconds) were rated as partially paralyzed.

Bracon venom and venom fractions cause a characteristic flaccid paralysis in lepidopteran larvae; the effects of purified fractions are identical to the effects of crude venom. In TBW and BAW larvae, there is no apparent difference between the effect of *B. hebetor* venom or venom fractions and the effects of *B. mellitor* venom or venom fractions. Affected larvae first become ataxic and stop feeding, then lose control of their appendages and show a lack of tone in the body wall musculature. This paralysis is characterized by the apparent loss of all voluntary motor functions. Involuntary functions, including gut peristalsis, heartbeats, and respiratory contractions, continue more or less normally and may persist for many days. Subparalytic doses caused a marked reduction in motor activity and cessation or sever inhibition of feeding. Thus, as previously noted by other researchers, Bracon venom is not lethal but rather immobilizes the "host" larva in a state suitable for consumption by the wasp. Extracts prepared from male wasps had no discernible biological effects.

PROTEIN PURIFICATION

Toxins from *Bracon hebetor* wasp venom were isolated using methods known in the art. Briefly, whole wasps or dissected venom glands and associated structures were homogenized and sonicated in order to solubilize the biologically active toxins. The homogenate was then centrifuged and the supernatant treated with polyethylene glycol to precipitate the active components. The precipitate was resuspended in starting buffer, and subjected to dye-ligand chromatography. The toxins were further purified by subjecting the biologically active fractions to immobilized-metal affinity chromatography, anion-exchange chromatography, size-exclusion chromatography, and reverse-phase chromatography. The reversephase chromatography yielded four fractions (numbers 4, 6, 7 and 9) which correspond to SEQ ID NO:1 (16 kDa toxin), the 18-1 toxin, the 18-2 toxin, and SEQ ID NO:2 (30 kDa toxin), respectively. A fifth component, with a molecular weight of approximately 20 kDa, coelutes with the 30 kDa component in fraction 9, but is separable by SDS-PAGE. Another protein purification technique used in connection with *Bracon mellitor* extracts is described in Example 18.

ANTIBODIES

Within the scope of this invention are included antibodies directed towards toxins SEQ ID NO:1 (16 kDa toxin), SEQ ID NO:2 (30 kDa toxin), the 18-1 toxin, and the 18-2 toxin, the 20 kDa toxin, and by extension, to similar toxins. Antibodies are proteins that are generated in animals and said to recognize or bind to a specific protein. When studying the insect toxins of this invention, it would be useful to be able to monitor the toxins' quantity, location and association with other proteins. Techniques such as Western blots, immunoprecipitation assays, and immunohistochemical assays cannot be performed without employing an antibody that specifically recognizes the peptide of interest.

In addition, antibodies can be used, by methods well known in the art, to purify and subsequently clone the proteins to which these toxins bind. This may be done by screening expression libraries, for example. Alternatively, these toxins may be purified by immobilizing the antibody to a solid support and by employing immunoaffinity chromatography.

Antibodies can be produced by a variety of methods well known in the art. Generally, antibodies are generated by immunizing a foreign animal (typically, rabbits or mice) with purified proteins. Insect toxins which are purified from whole wasp venom or tissue extracts, recombinantly expressed, or synthesized would be suitable for antibody production. The proteins induce an immune response in the animal, resulting in the production of many antibodies that recognize the protein. The sera of these animals contain polyclonal antibodies, which are a mixture of many antibodies that recognize the protein or a fragment or derivative thereof.

Alternatively, a single antibody, referred to as a monoclonal antibody, may be produced by hybridoma cloning technology well known in the art. See, Kennett, R. H. et al.

*Monoclonal Antibodies, Hybridomas: A New Dimension in Biological Analyses.* Plenum Press, New York, 1982. Briefly, the animal is immunized and the splenocytes of the animals are isolated and immortalized by fusing them with a suitable myeloma cell line. The cells are cloned by limited dilution. The cell lines that produce suitable monoclonal antibodies are kept and the remaining cell lines are discarded.

Thus, it is possible to produce antibodies to the toxins of this invention in order to facilitate further characterization, research, and development related to the use of the insecticidal toxins of interest.

cDNA ISOLATION AND CHARACTERIZATION

The SEQ ID NO:3 (16 kDa toxin cDNA) and SEQ ID NO:4 (30 kDa toxin cDNA) cDNA sequences were isolated by methods well known to those in the art. Generally, the N-terminal sequences of the 16 kDa toxin (SEQ ID NO:5) and the 30 kDa toxin (SEQ ID NO:6) were determined by chemical sequencing. Based on the genetic code and available codon usage data for insects, degenerate oligonucleotides complementary to the nucleic acid sequence encoding the amino acids of the protein were synthesized. The oligonucleotides were used in selective amplification of the mature toxin peptide beginning with amino acid residue 1, as shown in SEQ ID NO:3 (16 kDa toxin cDNA) and SEQ ID NO:4 (30 kDa toxin cDNA) cDNA sequences, by polymerase chain reaction techniques followed by cDNA library screening. The resulting products were confirmed by DNA sequencing.

PROTEIN MODIFICATIONS

Protein modifications can be subdivided into four general categories: chemical processing, additions, substitutions and deletions. These general groups apply to both the nucleic acid and amino acid sequences of the protein. While protein modifications may occur naturally, most often protein modifications are deliberately engineered into the nucleic acid sequence that codes for the protein. Protein modification techniques such as site-directed mutagenesis are well known in the art and in many cases are commercially available as kits complete with instructions from, for example, Amersham and Bethesda Research Laboratories.

Chemical processing generally occurs after protein translation, and includes modifications such as amidation, glycosylation, palmitoylation, and isomerization. Such processing events may be necessary for the stability and optimal activity of toxins (Heck et al., *Science,* 266: 1065–1068, 1994). The necessity and nature of these events, however, cannot always be predicted from chemical sequencing or translation of cDNA sequences.

A protein modification may occur through an addition. Additions as defined herein are modifications made to the nucleic acid or amino acid sequence which produce a protein containing at least one amino acid more than the primary amino acid sequence of the protein without significantly altering the function of the toxin. Naturally occurring nucleic acid additions in the coding region of the protein often severely impair the protein's function by causing a shift in the reading frame. From the point of the nucleotide addition, the amino acid sequence is entirely different than the primary amino acid sequence of the protein. It is possible, however, to have an addition within the coding region of the protein which does not change the reading frame of the protein. Nucleotide additions in the 5' or 3' untranslated region of the gene usually do not affect protein function.

As mentioned above, additions are usually deliberately engineered into the protein. In the present invention, for example, the mature protein lacks an initiator methionine which may be preferred for the efficient translation of the protein. Thus, the addition of a methionine to the amino terminus of the mature protein, as well as additions of other amino acids and nucleotides which facilitate the expression of the protein such as stop codons and ribosomal binding sites are included within the scope of this invention.

It is also understood that the addition of a signal sequence or signal peptide is included within the scope of this invention. Signal sequences direct protein transport to a particular location within the cell or organism. Alternatively, signal sequences may cause the protein to be secreted.

Comparison of all known signal peptides reveals that they are approximately 15–30 residues in length. Within the signal peptide there is a 7–13 residue stretch that constitutes a hydrophobic region (h-region). The h-region is rich in Ala, Met, Val, Ile, Phe and Trp, and occasionally contains Pro, Gly, Ser or Thr residues. von Heijne, G., *J. Mol. Biol.,* 184, 99–105 (1983). This sequence homology is shared from bacteria to higher eukaryotes, suggesting that the localization machinery is highly conserved. Proteins from one organism can be translocated and correctly processed by the localization machinery of several other organisms. Mueller et al., *J. Biol. Chem.,* 257, 11860–11863 (1982). Conversely, recombinant proteins comprising a signal peptide from one organism and a protein from a different organism are also properly localized. Yost et al. (1983); Jabbar & Nayak, *Mol. Cell. Biol.,* 7, 1476–1485 (1987). Studies suggest that signal sequences form their functional conformation independent of the remaining protein sequence which explains why signal sequences are readily interchangeable between different proteins and different species. In fact, studies performed using the scorpion peptide, AaIT, in baculovirus demonstrate that the addition of a signal sequence from one species to an insect toxin from another species is expected to succeed. The AaIT peptide was fused with the signal sequence from bombyxin, a secretory peptide from the silkworm Bombyx mori, and shown to secrete a functional AaIT peptide that was toxic to insects. McCutchen, B. F. et al., *Bio/Technology* 9, 848–852 (1991).

Finally, a secretory signal peptide may also greatly facilitate the purification of a peptide in an expression system by having the protein product secreted into the culture media rather than being retained by the host cell. In many instances the proteins are sufficiently pure in the media such that further purification is not required. This is particularly true for small proteins which are stable under a broad range of conditions.

Signal peptides for many prokaryotes, as well as eukaryotes and viruses are well characterized and documented in the literature. Thus, using basic recombinant DNA technology, such as PCR or synthetic oligonucleotides, a recombinant protein containing a signal peptide at its amino terminus can be easily engineered.

It is also understood that the addition of an antigenic epitope is included within the scope of the present invention. An epitope is a small, usually 6–20 amino acid residues, antigenic peptide for which a unique and specific antibody exists. Thus, by recombinantly engineering an antigenic epitope, the scientist is guaranteed a specific and effective antibody that will recognize the specific peptide. One such antigenic epitope is the c-myc epitope which has been recombinantly engineered into many proteins without any deleterious effect on function. Several other epitopes have been well documented in the literature and are commercially available along with the antibodies that recognize them.

Like the signal peptides, a recombinant protein containing an epitope can be engineered using common recombinant DNA technology. Unlike the signal peptide, however, the antigenic epitope may be engineered at the amino terminus or the carboxy terminus of the protein.

Protein modifications which occur through substitutions are also included within the scope of the invention. Substitutions as defined herein are modifications made to the nucleic acid or amino acid sequence of the protein, producing a protein which contains a different amino acid sequence than the primary protein without significantly altering the function of the toxin. Like additions, substitutions may be natural or artificial. It is well known in the art that amino acid substitutions may be made without significantly altering the protein's function. This is particularly true when the modification is the substitution of an amino acid for a "conserved" amino acid. Conserved amino acids are natural or synthetic amino acids which because of size, charge, polarity and conformation can be substituted without significantly affecting the structure and function of the protein. Frequently, many amino acids may be substituted by conservative amino acids without deleteriously affecting the protein's function.

Whether an amino acid can be substituted at all, or whether it can only be substituted by a conserved amino acid is best determined by comparing the specific peptide of interest with other wasp toxins. Amino acids that are identical in all the members of a protein family usually cannot be substituted. This is often the case with cystine residues which are critical for the formation of the protein's secondary structure. Amino acids which are conserved can usually be substituted by other conserved amino acids without significantly affecting the protein's function. Finally, amino acids which are not conserved within a family can usually be freely substituted.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the negatively charged amino acids Lys, Arg and His; the positively charged amino acids Asp and Glu, represent groups of conservative amino acids. This list is not exhaustive. For example, it is well known that Ala, Gly, Ser and sometimes Cys can substitute for each other even though they belong to different groups.

Conservative amino acid substitutions are not limited to naturally occurring amino acids, but also include synthetic amino acids. Commonly used synthetic amino acids are ω amino acids of various chain lengths and cyclohexyl alanine which are neutral non-polar analogs; citulline and methionine sulfoxide which are neutral non-polar analogs, phenylglycine which is an aromatic neutral analog; cysteic acid which is a positively charged analog and ornithine which is a negatively charged amino acid analog. Like the naturally occurring amino acids, this list is not exhaustive, but merely exemplary of the substitutions that are well known in the art.

Finally, protein modifications may occur through deletions. Deletions as defined herein are modifications made to the nucleic acid or amino acid sequence of the protein which produce a protein containing at least one amino acid less than the primary amino acid sequence of the protein, without significantly altering the function of the toxin. Like additions, naturally occurring deletions within the coding region of the protein usually severely impair the function of the protein, while deletions in the 5' and 3' untranslated region do not affect the function of the protein.

Deliberate deletions, however, may be required or useful for the expression of the protein in a foreign organism. For example, the cDNA sequences of SEQ ID NO:5 (16 kDa toxin NT) and SEQ ID NO:6 (30 kDa toxin NT) code for both the leader sequence and the mature protein. In the wasp the leader sequence is most likely removed by proteolysis as the precursor peptide is secreted. A deletion which removes the leader sequence from the precursor protein will, therefore, yield a functional mature protein similar to that secreted by the wasp. Accordingly, deletion of the leader sequences, as well as other deletions which facilitate the expression of the toxins are to be included within the scope of the invention.

RECOMBINANT EXPRESSION

Once the cDNA has been recombinantly modified to express a protein suited for a particular need, the cDNA, including all modifications, is subcloned into an expression vector. In general, expression vectors are like plasmids which additionally contain a promoter, a termination signal and sometimes a selectable marker. Any expression vector containing a prokaryotic, eukaryotic or viral promoter and a termination signal is included within the scope of the invention.

A promoter is a nucleic acid sequence, generally engineered 5' to the cDNA, which recruits and directs the transcription of RNA using the cDNA as a template. From this transcribed RNA message, the cell can assemble the protein which is encoded by the cDNA through a process known as translation.

Promoters can generally be classified as constitutive, inducible, or tissue specific. A constitutive promoter is a promoter which is not regulated to a significant extent by any cellular factors and continually directs the transcription of the RNA. These promoters are used when large quantities of protein are desired. The cytomegalovirus promoter and the Rous Sarcoma virus promoters are examples of constitutive eukaryotic promoters. The int promoter of bacteriophage l and the bla promoter of β-lactamase are examples of constitutive prokaryotic promoters.

Included in this group are promoters which are characterized as early or late promoters. These promoters are usually viral promoters which are activated to high levels either early or late in viral replication. The baculovirus p10 and polyhedrin promoters are examples of late promoters.

Inducible promoters are promoters that are induced or repressed by certain factors. These promoters allow regulation of the amount of protein produced, and the timing of such production. Examples of inducible promoters are the eukaryotic metallothionine promoter which is induced by increased levels of heavy metals and the prokaryotic lacZ promoter which is induced in response to isopropyl β-D-thiogalacto-pyranoside (IPTG).

Finally, tissue specific promoters are promoters which only function in a particular cell type. These promoters are usually used when expression of the protein in all cell types is harmful to the organism. An example of a mammalian tissue specific promoter is the skeletal muscle creatine kinase promoter.

An expression vector also requires a termination signal. The termination signal is usually engineered 3' to the protein of interest. In higher eukaryotes, for example, the expression vector must contain a polyadenylation signal in order for the transcript to be translated into a protein. A termination signal like the adenovirus polyadenylation signal and the baculovirus polyhedrin polyadenylation signal may be used. Alternatively, peptide's own polyadenylation signal may serve as an efficient termination signal.

In most instances, the expression vector also requires a selectable marker which allows for the identification of cells which have actively incorporated the expression vector. These selectable markers are genes whose protein product confers resistance to an antibiotic or other chemical. Thus, cells that are capable of growing in the presence or absence of a certain chemical are known to contain the expression vector. Examples of selectable markers are the β-lactamase gene which confers resistance to ampicillin in prokaryotes and the neomycin gene which confers resistance to G-418 in eukaryotic cells. An expression vector is not limited to one selectable marker and, in fact, most expression vectors contain multiple selectable markers.

In short, the availability and knowledge of prokaryotic and eukaryotic promoters, termination signals and selectable markers is well known in the art. In fact, many types of expression vectors for bacterial, yeast, mammalian and viral expression systems are commercially available.

RECOMBINANT HOSTS

The desired expression vector, including the cDNA, is then transformed or transfected into the host cell or organism. Both transformation and transfection refer to the incorporation of the expression vector into a host by methods such as electroporation or calcium phosphate treatment which are well known in the art. Like plasmids, expression vectors may remain episomal or be incorporated as part of the host's genome. Incorporation into the host genome can be accomplished by either random integration or homologous recombination. Random integration results in the insertion of multiple genes in unknown locations of the host's genome, while homologous recombination results in the insertion of one copy of the gene in a known location of the host's genome. The above techniques are expected to be useful for the expression of the toxins of this invention and are included within the scope of the invention.

Recombinant hosts are chosen based on the goals to be achieved. For the purposes of expressing an insecticidally effective protein there are two general types of hosts which are particularly useful: hosts that are useful for isolating large quantities of recombinant proteins, and hosts that infect insect pests.

Bacteria, particularly *E. coli*, are still the most commonly used host for the isolation of large quantities of recombinant proteins. A recombinant bacterial host expressing an insect toxin, therefore, is expected to be a useful technique for isolating the insect toxins of the present invention for use as insecticides. The toxin may be fused to a signal peptide as described above or expressed as a mature protein. Bacterial overexpression systems are well known in the art and are commercially available.

The toxins expressed in a bacterial overexpression system, however, will not contain post-translational modifications. Therefore, baculovirus infected insects or insect cell lines are frequently employed to isolate large quantities of post-translationally modified proteins. A wide variety of prokaryotic and eukaryotic proteins have been successfully expressed in baculovirus. Luckow, V. and Summers, M., *Bio/Technology,* 6, 47–55 (1988); Summers, M. D. and Smith, G. E., *Texas Agricultural Experimental Station Bulletin,* 1555, 1–56 (1987).

As in bacterial hosts, recombinant baculoviruses may express proteins as either fusion or mature proteins. Expression of foreign genes in this system has been known to yield as much as 500 mg/liter of protein. Because insect cells are eukaryotic, the recombinant proteins produced using baculovirus infected insect cells are very similar to the native proteins. Studies have shown that recombinant proteins expressed by a baculovirus vector may be secreted, localized to the nucleus, localized to the cell surface, disulfide-linked, proteolytically cleaved, phosphorylated, N-glycosylated, O-glycosylated, myristylated or palmitylated. Luckow, V. and Summers, M. *Bio/Technology* 6, 47–55 (1988).

The recombinant peptide isolated from these hosts may be applied directly to the plants or animals sought to be protected from the insect pests. As discussed later, the recombinant virus itself may be used as a pest control agent.

Alternatively, the recombinant peptide will be used to study the physiological mechanism which leads to the paralysis of insect pests. Given the mechanism of action of other arthropod toxins, it is likely that the toxins of interest herein act by altering the function of neurons. Studies with partially purified *Bracon venom* components have suggested that these materials inhibit neurotransmitter release at the neuromuscular junction. Moreover, prior art and the data in this specification strongly suggest that these toxins are highly selective for insect pests, displaying negligible mammalian toxicity. This is true despite the fact that mammalian neurons are well known to be susceptible to toxins which inhibit or enhance neurotransmitter release. Therefore, toxins, such as the toxins of this invention, may be used to help elucidate and characterize the differences between the insect and vertebrate forms of their respective target sites. This information can then be used in chemical design studies aimed at developing chemical insecticides which are highly selective for insect pests.

Pathogens infecting insects represent a second class of recombinant hosts useful for the expression of the subject peptides. From an agricultural standpoint, bacteria and baculoviruses are the most promising pathogen candidates, although pathogenic fungi might also be used for this purpose.

Certain bacteria pathogenic to insects, especially *Bacillus thuringiensis* (B. t.), have been used to control a variety of insect pests. Unfortunately, naturally occurring pathogens often have limited utility as biological insecticides due to limitations in delivery, toxicity and speed of action. Current work, however, has demonstrated that B.t. may be engineered to produce a recombinant bacterium which overcomes some of the limitations of the wild-type B.t. Most notably, the B. t. delta-endotoxin gene has been engineered into bacterial pathogens to produce hybrid hosts which display superior insecticidal properties. Similarly, the production of recombinantly engineered bacterial or fungal pathogens which express the toxins of this invention are thought to be useful and thus included within the scope of the invention.

Wild-type baculoviruses are also natural regulators of many different types of insects pests, including *Heliothis virescens* (tobacco budworm), *Orgyia pseudotsugata* (Douglas fir tussock moth) and *Laspeyresia pomonella* (codling moth). See Gröner, A. 1986. Specificity and Safety of Baculovirus. Vol I *Biological Properties and Molecular Biology*. Granados, R. R. and Federici, B. A. eds. CRC Press, Inc. Boca Raton, Fla. Baculoviruses, such as *Autographa californica* nuclear polyhedrosis virus, produce post-infection viral progeny: extracellular viral particles and occluded viral particles. The occluded viral particles are important because they provide a means for horizontal and vertical transmission. After infected insect pests die, millions of viral particles are left behind protected by the viral occlusion. Thus, when insect pests feed on contaminated plants, they ingest the occlusion bodies. The occlusion bodies dissolve in the alkaline environment of the insect gut releasing the viral particles which infect and replicate in the insect's midgut tissue. Secondary infection within a host is spread by extracellular, non-occluded viral particles.

Unfortunately, insects infected by baculoviruses may take a week or more to die and continue to feed for much of that time, making the commercial use of wild-type baculovirus commercially infeasible. It has been shown, however, that baculoviruses, such as the *Autographa californica* nuclear polyhedrosis virus, can be recombinantly engineered to express an insecticidal toxin, thus accelerating their pathogenic effects. McCutchen, B. F. et al., *Bio/Technology,* 9, 848–852 (1991); Tomalski et al., *Nature,* 352, 82–85 (1991); Stewart et al., *Nature,* 352, 85–88 (1991). A recombinant vector, pAcUW2(B).AaIT, was constructed containing a polyhedrin gene driven by the polyhedrin promoter and the AaIT insect toxin driven by the p10 promoter. The resulting recombinant baculovirus was orally infective under normal conditions. Furthermore, the AaIT toxin was secreted in the course of infection and caused paralysis of both *Manduca sexta* larvae, an unnatural host for the virus, and *Heliothis virescens* larvae, a natural host.

Using basic recombinant technology well known in the art, it is expected that the toxins of the present invention may similarly be recombinantly engineered to produce a recombinant baculovirus which would display increased host range and toxicity. Recombinant baculoviruses expressing the toxins of this invention, like current insecticides, could then be administered to the crops sought to be protected from insect pests. The release of recombinant baculoviruses into the environment is expected to be a safe and effective means of controlling insect pests. First, naturally occurring insecticidal toxins are highly selective. In addition, baculoviruses do not infect mammals and are highly selective within an insect group. Therefore, by carefully selecting the baculovirus host and insecticidal peptide, it is possible to engineer recombinant baculoviruses which are highly selective for the target insect pest while simultaneously reducing the impact on non-targeted organisms, including beneficial insects. Second, recombinant baculoviruses, in the absence of strong selective pressure, are likely to revert back to the wild-type after a short time of being exposed to environmental pressures. Thus, the relatively short life of the recombinant baculoviruses further reduces the risk to non-targeted species.

The quantity and frequency of recombinant baculovirus application will necessarily depend on such things as the particular crop being protected, the insect pest and the climate. Accordingly, the quantity and frequency of recombinant baculovirus application is best determined empirically.

EXAMPLES

The following examples are given to illustrate various embodiments which have been made or may be made in accordance with the present invention. These examples are given by way of example only, and it is to be understood that the following examples are not comprehensive or exhaustive.

Example 1

Bioassays: Extracts from whole wasps, *Bracon hebetor*, or from the biologically active fractions obtained during purification, were dissolved in the desired volume of phosphate buffered saline or other buffers used in the course of venom fractionation. Samples were administered by injection into the abdomen of fifth instar larvae of the tobacco budworm, *Heliothis virescens*, as previously described. Control larvae were injected with equal volumes of the appropriate buffer.

When extracts or active fractions were injected into *H. virescens* larvae, affected larvae first became ataxic and stopped feeding, then lost control of their appendages and showed a lack of tone in the body wall musculature. This paralysis was characterized by the apparent loss of all voluntary motor functions. Involuntary functions, including gut peristalsis, heartbeats, and respiratory contractions, continued more or less normally and often persisted for many days. Subparalytic doses caused a marked reduction in motor activity and cessation or sever inhibition of feeding. Control larvae were unaffected.

The table below summarizes the toxicity of whole wasp extract and of the biologically active fractions obtained during the purification procedure.

TABLE I

| Sample | Volume (ml) | Protein (mg) | Fold Purification wt/wt[a] | Dilution for TWB assay | Final Volume[b] | TBW Paralysis[c] |
|---|---|---|---|---|---|---|
| Whole Extract | 135 | 952 | 13.5 | 1:20 | 2700 | 2P,1NE |
|  |  |  |  | 1:30 | 4050 | 1P,2NE |
| PEG Supernatant | 270 | 618 | — | 1:5 | 1350 | 3NE |
| Solubilized PEG Precipitate | 40 | 272 | 47 | 1:60 | 2400 | 1P,1PP, 1FI |
| Matrex Red Pooled Fractions | 80 | 42.4 | 304 | 1:30 | 2400 | 2P,1NE |
| IMAC Pooled Fractions | 4.2 | 8.3 | 1552 | 1:500 | 2100 | 2P,1NE |
| AX Pooled Fractions | 0.9 | 2.9 | 4396 | 1:2000 | 1800 | 3P |
|  |  |  |  | 1:3000 | 2700 | 2P,1NE |
| SE-AX Pooled Fractions[d] | 2.3 | 0.38 | 33915 | 1:400 | 920 | 2P,1NE |
|  |  |  |  | 1:800 | 1840 | 1P,1PP, 1FI |

[a]Fold purification calculated from 12.88 grams of whole wasps
[b]Final volume = volume of sample × dilution for TBW assay
[c]P = paralyzed, PP = partially paralyzed, FI = feeding inhibited, NE = no effect
[d]This sample is also identified herein as "Bracon toxin actives"
Matrex Red = Matrex Red A Affinity column
IMAC = Immobilized-metal affinity chromatography
AX = Anion-exchange chromatography
SE-AX = Size-exclusion and anion-exchange chromatography The paralytic activity of the toxins is destroyed under acidic conditions. Therefore, the fractions from the final chromatographic step were not bioassayed.

Example 2

Purification of SEQ ID NO:1 (16 kDa toxin): The wasp extract was fractionated by high performance liquid chromatography, incorporating Beckman System Gold 126 solvent delivery and 168 photodiode-array detector modules. The Bracon toxins are most stable between pH 8 and 9; exposure to ph<7 results in rapid loss of activity. The toxins are more stable at 4° C. than at 0° C. once they are in solution. Therefore, fractions were stored in the refrigerator during the purification.

*Bracon hebetor* whole wasps were stored frozen at −70° until used. Frozen wasps (12.88 g; a mixture of male and female wasps) were mixed with 60 ml of cold (4° C.) 50 mM sodium monophosphate, adjusted to pH 8.1 with sodium hydroxide, and homogenized with a Tissue-Tearor homogenizer (Biospec Products, Inc.). The homogenates were then sonicated for 20 sec at 4° C. (VirSonic 475; Virtis) and centrifuged at 19,000 rpm (Sorvall SS-34 rotor) for 20 min. The bioactive supernatant was saved. The pellet was extracted twice more, with 35 ml of cold buffer each time, as described above. Supernatants from all three of the extractions were combined and centrifuged a final time for 20 min at 19,000 rpm to clarify. To the cold clarified supernatants (135 ml) was added an equal volume of 60%. polyethylene glycol (w/v in water, 3350 average molecular weight; Sigma Chemical Co.). The mixture was swirled and allowed to stand on ice for 40 min to precipitate the bioactive proteins. The mixture was then centrifuged at 19,000 rpm for 20 min. The inactive supernatant was discarded and the excess polyethylene glycol rinsed from the centrifuge tubes with 2 ml of water, without dissolving the pellet. The bioactive pellet was then resuspended in 24 ml of the starting buffer and the suspension was spun at 19,000 rpm for 20 min. The cloudy supernatant, which contains the bioactivity, was filtered through several Acrodisc PF filters (0.8/0.2 μm filters; Gelman Sciences) and the filters were rinsed with a total of 2 ml of buffer. The pellet was resuspended in 10 ml of buffer followed by centrifugation at 19,000 rpm for 15 min and filtration as described above.

Figure 1:
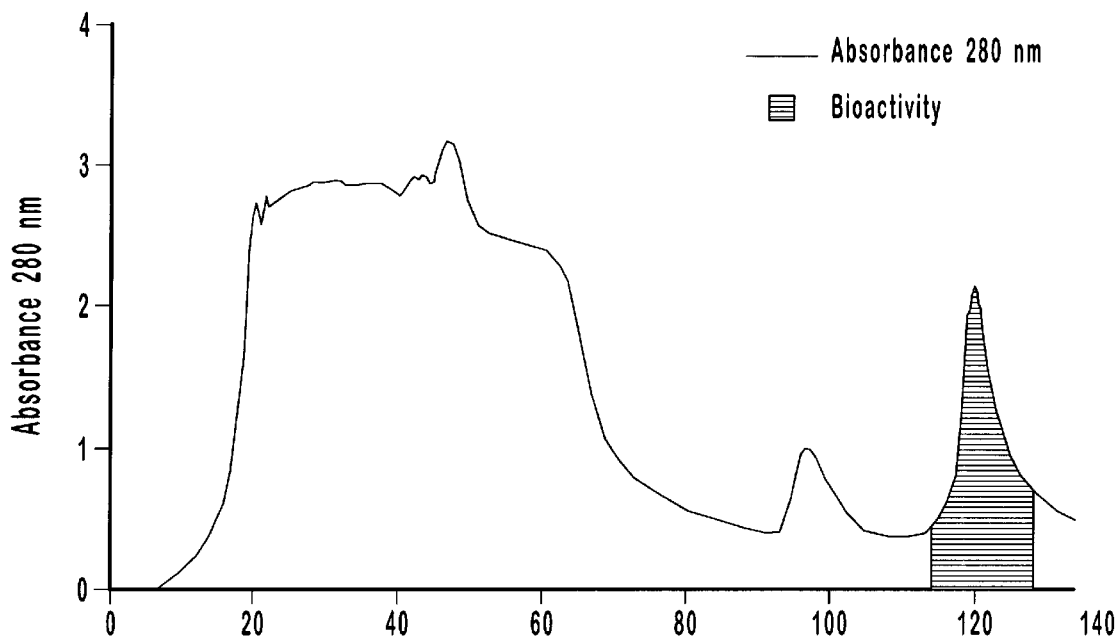
FIG. 1 is a chromatogram of an extract of *Bracon hebetor* wasps subjected to dye-ligand chromatography on a Matrex Red A affinity column and illustrates the biologically active peak eluted between approximately 115–129 minutes.

The combined filtrate (40 ml) was subjected to dye-ligand chromatography on a Matrex Red A affinity column (2.6×18 cm; Amicon) equilibrated in 50 mM sodium monophosphate, adjusted to pH 8.1 with sodium hydroxide. The sample was loaded onto the column at a flow rate of 1.5 ml/min and the effluent was monitored at 280 nm. After loading, the column was rinsed with ~100 ml of the same buffer at a flow rate of 3 ml/min. The column was then eluted, stepwise, with 165 ml of 300 mM NaCl in the phosphate buffer, followed by 160 ml of 2M NaCl in the phosphate buffer, at a flow rate of 4 ml/min (as illustrated in FIG. 1). The bioactivity eluted as a broad peak in the 2M NaCl wash as noted on the chromatogram. These fractions were collected into 15 ml tubes that contained 1.5 ml of 0.5M sodium borate, pH 9.0 to improve the stability of the bioactive component(s). The active fractions were pooled and adjusted to 1 mM with imidazole in preparation for immobilized-metal affinity chromatography (IMAC).

Figure 2:
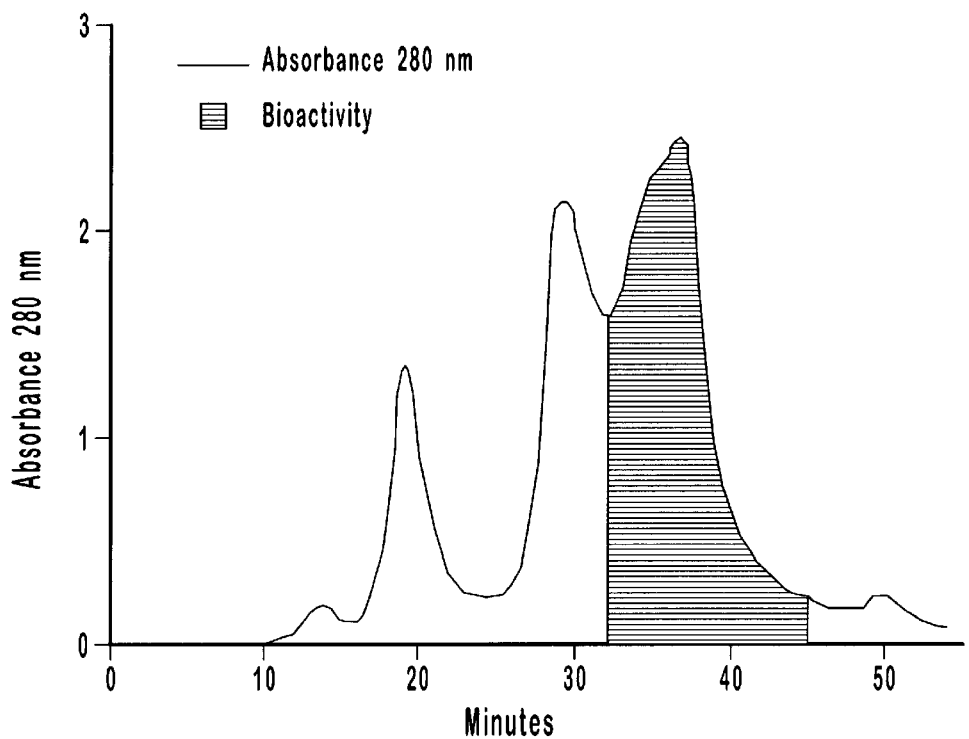
FIG. 2 is a chromatogram of pooled active fractions from FIG. 1 subjected to chromatography on a TSK Chelate-5PW column and illustrates the biologically active peak eluted between approximately 31–45 minutes.

The red column pool (80 ml) was chromatographed on two TSK Chelate-5PW columns in series (each 7.5×75 mm; TOSOHAAS). The columns had been stripped with EDTA and freshly loaded with $Cu^{+2}$ (Belew, M., et al. (1987) *Anal. Biochem.* 164, 457–465). Buffer A was 1 mM imidazole, 50 mM sodium borate, 0.5M sodium chloride, pH 9.0; buffer B was 50 mM imidazole, 50 mM sodium borate, 0.5M sodium chloride, pH 9.0. After the sample was loaded onto the column at a flow rate of 1 ml/min, and the absorbance (280 nm) had returned to baseline, the column was developed with 12 ml of 5% B, followed by a 10 min linear gradient from 5 to 30% B and a 10 min linear gradient from 30 to 100% B (as illustrated in FIG. 2). The effluent was monitored at 280 nm and fractions were collected and assayed for paralytic activity. The active fractions, eluting between 32 and 45 min, were pooled. The pool was concentrated and exchanged into 50 mM borate, pH 9.0, by ultrafiltration in two, Centricon-30 filters (30,000 MWCO filter; Amicon), in preparation for ion-exchange chromatography.

Figure 3:
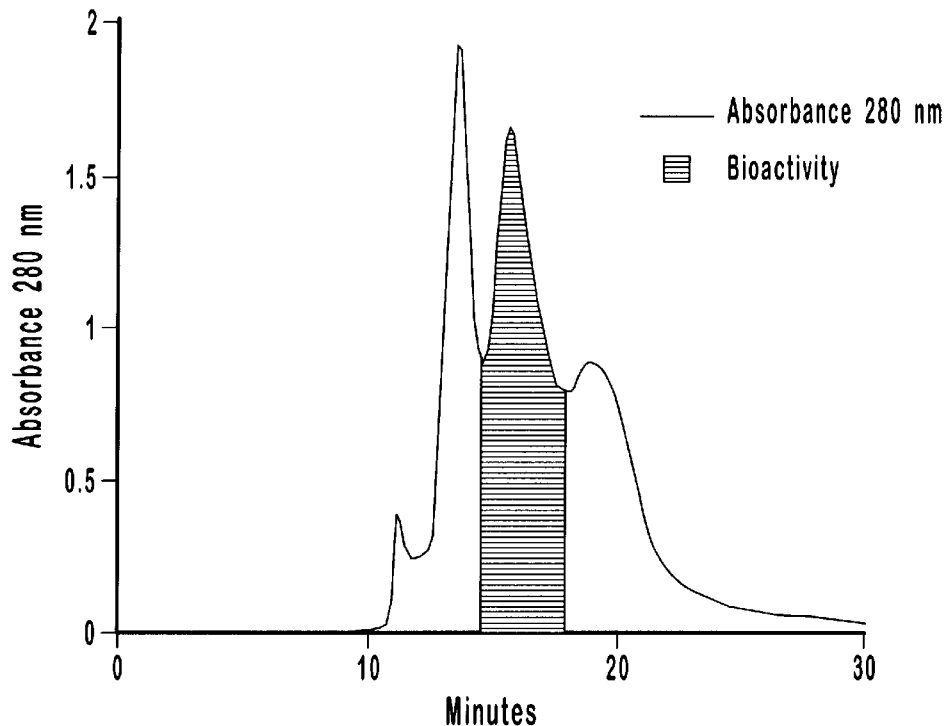
FIG. 3 is a chromatogram of the pooled active fractions from FIG. 2 subjected to anion-exchange chromatography on a Fractogel EMD TMAE-650 column and illustrates the biologically active peak eluted between approximately 14.5–18 minutes.

Anion-exchange (AX) chromatography was performed on a Fractogel EMD TMAE-650 column (1×7 cm, 25–40 μm particle size; EM Separations Technology). The concentrated IMAC pool (4 ml) was diluted to 16 ml with 50 mM sodium borate, pH 9.0 and loaded onto the anion-exchange column. The column was rinsed with 15 ml of the starting buffer. After the 280 nm absorbance had returned to baseline, the column was developed with a 37.5 min linear gradient from 0 to 1M NaCl in 50 mM sodium borate, pH 9.0. The flow rate was 1.5 ml/min, the effluent was monitored at 280 nm (as illustrated in FIG. 3) and fractions were collected and assayed for bioactivity. The fraction eluting between 14.5 and 17.5 min was the most active, but the final peak also showed a small amount of activity. The most active fraction (14.5–17.5 min) was concentrated to ~0.9 ml in a Centricon-3 filter (3000 MWCO filter; Amicon). The sample was then adjusted to pH 7.2 by addition of 90 μl of 0.2M sodium monophosphate in preparation for size-exclusion (SE) chromatography.

Figure 4:
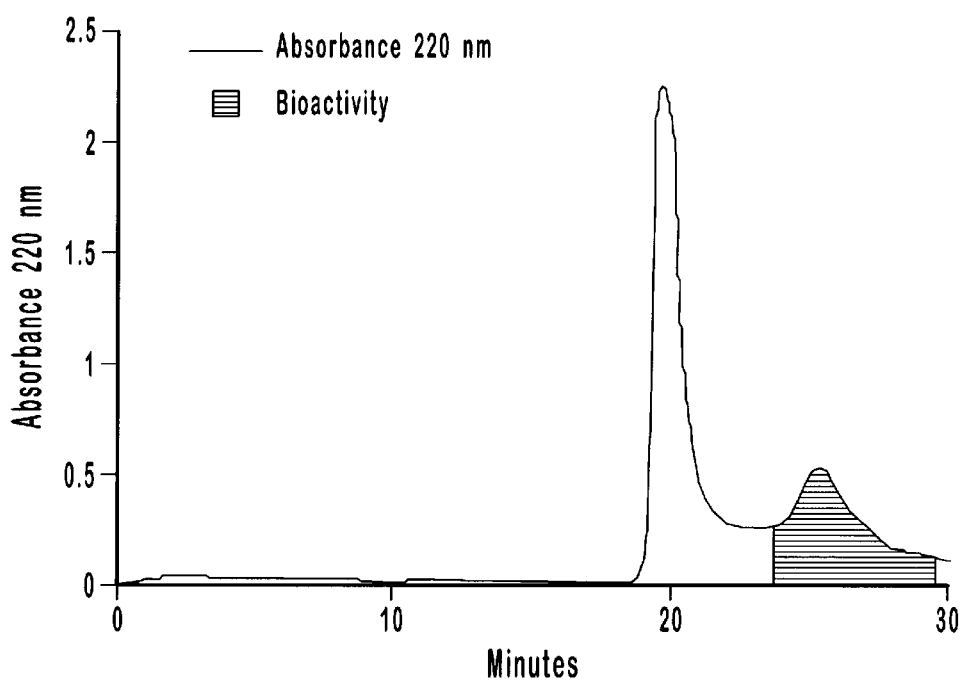
FIG. 4 is a chromatogram of the pooled active fractions from FIG. 3 subjected to size-exclusion chromatography on a TSK G2000SW column and illustrates the biologically active peak eluted between approximately 24–29 minutes.

The concentrated anion-exchange pool (990 μl) was chromatographed on a TSK G2000SW column (21.5×60 cm, 13 μm particle size; TOSOHAAS). The column was developed with 50 mM sodium monophosphate, 150 mM sodium chloride, adjusted to pH 7.0 with sodium hydroxide. The flow rate was 5 ml/min, the effluent was monitored at 220 nm and fractions were collected as noted on the chromatogram (FIG. 4). To each ~10 ml fraction was added 1.0 ml of 0.5M sodium borate, pH 9.0, to improve stability of the toxins. The first peak of material contains a protein of ~80 kDa (from SDS-PAGE). This protein shows no activity by itself, but seems to stabilize the Bracon toxins, as the activity becomes more labile (both to storage at 4° C. and to subsequent chromatographic steps) after this step. The fractions eluting between 24 and 29 min showed appreciable activity, with the peak of the activity in the latter half of the peak (26–29 min) . The active fractions were combined (27 ml) and diluted to 100 ml with 50 mM sodium borate, pH 9.0, in preparation for concentration by anion-exchange chromatography.

The diluted pool from the size-exclusion chromatography was loaded onto a Fractogel EMD TMAE-650 column (0.5×5 cm, 25–40 $\mu$m particle size), at a flow rate of 1.0 ml/min, and the column rinsed with 10 ml of 50 mM sodium borate, pH 9.0. The column was then rinsed with an additional 2.5 ml of the starting buffer, followed by a 37.5 min linear gradient from 0 to 1M NaCl in 50 mM sodium borate, pH 9.0. The flow rate was 0.5 ml/min and the effluent was monitored at 280 nm. Fractions were collected (as illustrated in FIG. 5) and assayed for paralytic activity. The active fractions were combined and subjected to reversed-phase chromatography. This active pool is identified as "Bracon toxin actives".

The active pool from above (2 ml) was adjusted to 0.1% in TFA to lower the pH and loaded onto a Vydac C4 column (300 Å, 4.6×50 mm; The Separations Group) equilibrated in 5% acetonitrile in water, in constant 0.1% TFA. After loading, the column was stepped to 20% acetonitrile in water, in constant 0.1% TFA and then developed with a 15 min linear gradient from 20–80% acetonitrile in water, in constant 0.1% TFA. The flow rate was 1 ml/min, the effluent was monitored at 220 nm and fractions were collected as noted on the chromatogram. Fraction 4 contained SEQ ID NO:1 (16 kDa toxin) as determined by SDS-PAGE (12.5% acrylamide) and N-terminal sequence analysis. Approximately 16 $\mu$g of SEQ ID NO:1 was recovered from 12.88 g of whole wasps.

Example 3

Purification of SEQ ID NO:2 (30 kDa toxin): SEQ ID NO:2 was isolated by the same protocol used to purify SEQ ID NO:1 described in Example 2, except that SEQ ID NO:2 eluted in fraction 9 of the final chromatographic step. SEQ ID NO:2 had a molecular weight of 30 kDa as determined by SDS-PAGE (12.5% acrylamide). Approximately 54 µg of SEQ ID NO:2 was recovered from 12.88 g of whole wasps. SDS-PAGE also indicated that a protein of approximately 20 kDa co-eluted with the 30 kDa protein. Only one sequence was seen by N-terminal sequence analysis of fraction 9, and that sequence agreed with the sequence obtained by analyzing an SDS-PAGE-purified sample of the 30 kDa protein.

Example 4

Purification of the 18-1 toxin: The 18-1 toxin was isolated by the same protocol used to purify SEQ ID NO:1 (16 kDa toxin) described in Example 2 except that the 18-1 toxin eluted in fraction 6 of the final chromatographic step. The 18-1 toxin had a molecular weight of 18 kDa as determined by SDS-PAGE (12.5% acrylamide). Approximately 28 µg of the toxin was recovered from 12.88 g of whole wasps.

Example 5

Purification of the 18-2 toxin: The 18-2 toxin was isolated by the same protocol used to purify SEQ ID NO:1 (16 kDa toxin) described in Example 2, except that the 18-2 toxin eluted in fraction 7 of the final chromatographic step. The toxin had a molecular weight of 18 kDa as determined by SDS-PAGE (12.5% acrylamide). Approximately 18 µg of the 18-2 toxin was recovered from 12.88 g of whole wasps.

Example 6

N-terminal Amino Acid Sequencing of SEQ ID NO:1 (16 kDa toxin) : N-terminal amino acid sequence analysis of the SEQ ID NO:1 (16 kDa toxin) was performed at the Biotechnology Center of Utah State University. The N-terminal sequence (SEQ ID NO:5) is shown below:

```
Phe Asn Pro Glu Thr His Arg Glu Xaa Lys Asn Tyr Xaa Ala Lys
1               5                   10                  15
Glu His Gly Glu Glu Tyr Arg
                20
``` where Xaa signifies residues that were not determined by chemical sequencing.

Example 7

N-terminal Amino Acid Sequencing of SEQ ID NO:2 (30 kDa toxin) : N-terminal amino acid sequence analysis of the SEQ ID NO:2 (30 kDa toxin) was performed at the Biotechnology Center of Utah State University. The N-terminal sequence (SEQ ID NO:6) is shown below:

```
Ile Ile Asn Gly His Asp Ala Thr Glu Gly Gln Phe Pro His Met
1               5                   10                  15
Ala Tyr Leu Gln Ala Ser Ala Gly
                20
```

Example 8

N-terminal Amino Acid Sequencing of the 18-1 toxin: N-terminal amino acid sequence analysis of the reduced, derivatized 18-1 toxin was performed at the Biotechnology Center of Utah State University. The N-terminal sequence (SEQ ID NO:7) is shown below:

```
Thr Leu Phe (Leu/Gly) Ala Pro (Lys/Ala) Phe (Cyc/Asn) Gly
1           5                                         10
Arg (Ala/Cys) Asp Lys Thr Phe Gly (Tyr/Pro) Gln Arg
                  15                            20
Phe Glu Gly Asp Val Gly
21              25
```

The second amino acid in each parenthesis was seen as a minor component at that sequencing step. This may indicate some heterogeneity in this protein sample.

Example 9

N-terminal Amino Acid Sequencing of the 18-2 toxin: N-terminal amino acid sequence analysis of the 18-2 toxin peptide was performed at the Biotechnology Center of Utah State University. The sequence (SEQ ID NO:8) is shown below:

```
Thr Leu Phe Thr Asp Arg Lys Trp Xaa Gly Arg Ala Asp Lys Thr
1               5                   10                  15
Phe Gly Pro Ser Arg
                20
``` where Xaa signifies residues that were not determined by chemical sequencing.

Example 10

Degenerate Oligonucleotide Complementary to SEQ ID NO:5 (16 kDa toxin NT) : Based on the genetic code and available codon usage data, a degenerate oligonucleotide complementary to the nucleic acid sequence which coded for SEQ ID NO:5 (16 kDa toxin NT) was synthesized. The oligonucleotide sequence (SEQ ID NO:9) is shown below:

TTCAAYCCNG ARACNCATMG NGA where, A=adenine, T=thymidine, C=cytosine, G=guanine, Y=C or T, R=G or A, M=A or C, and N=A or G or T or C.

Example 11

Degenerate Oligonucleotides Directed at SEQ ID NO:6 (30 kDa toxin NT): Based on the genetic code and available codon usage data, two degenerate oligonucleotides complementary to the nucleic acid sequence which coded for SEQ ID NO:6 (30 kDa toxin NT) were synthesized. The first degenerate oligonucleotide (SEQ ID NO:10) was made complementary to residues 1–7 and the second degenerate oligonucleotide (SEQ ID NO:11) was made complementary to residues 7–16.

SEQ ID NO: 10: ATYATYAACG GNCAYGAYGC    20

SEQ ID NO: 11: GCYACNGAGG GNCAGTTYCC ICMNATGGC 29 where, A=adenine, T=thymidine, C=cytosine, G=guanine, I=inosine, Y=C or T, M=A or C, and N=A or G or T or C.

Example 12

Isolation of the SEQ ID NO:3 (16 kDa toxin cDNA): Total RNA was isolated by method of Chomczynski and Sacchi, *Analytical Biochemistry* 162, 156 (1987). Briefly, the venom glands and associated tissues were homogenized in guanidinium thiocyanate. The homogenized tissue was then extracted with water equilibrated phenol and chloroform until the interphase between the aqueous and organic phase was clear. The aqueous layer was precipitated with ethanol and the total RNA was recovered by centrifugation. Polyadenylated RNA (mRNA) was isolated using oligo d(T) cellulose chromatography kits purchased from Pharmacia.

Thereafter, fifty nanograms of mRNA were used as a template for the synthesis of cDNA. An oligonucleotide containing a string of 15 thymidine residues and additionally containing a Not I endonuclease recognition signal (hereafter $d(T)_{15}$) was allowed to hybridize to the mRNA. The cDNA was synthesized by Moloney murine leukemia virus reverse transcriptase under the conditions prescribed by the manufacturer, Bethesda Research Laboratories (BRL).

Selective amplification of the SEQ ID NO:3 (16 kDa toxin cDNA) was achieved by the PCR-RACE technique described by Frohman using the oligonucleotides $d(T)_{15}$ and SEQ ID NO:9 described in Example 10. Frohman, M. A., *PCR protocols*, ed. Innis et al., Academic Press, San Diego, Calif., (1990). The PCR-RACE was performed using one-fourth of the cDNA obtained in the previous step; 2 μM final of SEQ ID NO:5 and $d(T)_{15}$; 100 μM final of each deoxynucleotide triphosphate; and 4 units of AmpliTaq DNA polymerase purchased from Perkin Elmer. Initially two cycles of the polymerase chain reaction were carried out, each cycle comprising a denaturation step at 94° C. for 2 min. followed by a primer annealing step at 40° C. for 2 min. and a primer extension step at 72° C. for 1 min. This was followed by 28 cycles carried out by a denaturation step at 95° C. for 1 min. followed by a primer annealing step at 56° C. for 1 min. and a primer extension step at 72° C. for 1 min.

Anchored PCR products were visualized on a 1% NuSieve/0.5% SeaKem composite agarose gel (FMC, Rockland, Me.). The resulting amplified cDNAs were excised from the gel and purified using glassmilk resin supplied in the Geneclean® kit (Bio101, Vista, Calif.). Inserts were digested with restriction enzyme Not I and the pSK vector (Stratagene, La Jolla, Calif.) was digested with Not I and Eco RV. The cDNA was then ligated into the pSK vector and transformed into the bacterial strain DH5αF' (Life Technologies, Inc., Gaithersburg, Md.).

Confirmed cDNA subclones were used to screen a cDNA library using methods well known in the art. The complete cDNA sequence is SEQ ID NO:3 (16 kDa toxin cDNA).

Example 13

Isolation of the SEQ ID NO:4 (30 kDa toxin cDNA): The SEQ ID NO:4 (30 kDa toxin cDNA) was isolated by the same protocol described in Example 12 for SEQ ID NO:3 (16 kDa toxin cDNA), except the degenerate oligonucleotides used for PCR-RACE were SEQ ID NO:10 and SEQ ID NO:11, as described in Example 11, rather than the oligonucleotide described in Example 10.

Example 14

Recombinant Baculovirus Harboring SEQ ID NO:3 (16 kDa toxin cDNA): A plasmid harboring the SEQ ID NO:3 (16 kDa toxin cDNA), or any modification thereof, is digested with endonucleases that release the cDNA from the plasmid. The cDNA can then be run and isolated from an agarose gel using any of several methods well known in the art. If, for example, the baculovirus expression vector employed for the expression of AaIT toxin is used, the cDNA is blunted with either the large fragment of DNA polymerase I or T4 DNA polymerase, depending on the overhang left by the endonuclease used above. Bam HI linkers are then ligated to both ends of the cDNA. The expression vector pAcUW2 (B) is then digested with Bgl II endonuclease and dephosporylated with calf intestine alkaline phosphatase or other phosphatase. McCutchen, B. F. et al. *Bio/Technology* 9, 848–852 (1991). The purified Bam HI linked SEQ ID NO:3 (16 kDa toxin cDNA) and pAcUW2 (B) is then ligated to form the completed SEQ ID NO:3 (16 kDa toxin cDNA) expression vector. Detailed instruction for all the techniques used above may be found in Maniatis et al., *Molecular Cloning a Laboratory Manual*, Cold Spring Harbor Laboratory, Cold Spring Harbor, (1982), or similar manual.

Next, Sf-9 cells (ATCC#CRL1711) are co-transfected by calcium precipitation with the SEQ ID NO:3 (16 kDa toxin cDNA) expression vector and a polyhedrin-negative *Autographa californica* nuclear polyhedrosis virus (AcNPV) DNA, such as the RP8 transfer vector. Matsuura et al., *J. Gen. Virol* 68: 1233–1250 (1987). The supernatant is isolated 5 days post-transfection and subjected to plaque purification. The homologously recombined recombinant baculovirus forms polyhedrin-negative plaques that are isolated and purified according to the method of Summers and Smith. Summers, M. D. and Smith, G. E., *Texas Agricultural Experimental Station Bulletin,* 1555, 1–56 (1987).

The purified recombinant plaques are then tested for biological activity. Proliferating Sf-9 cells are infected with recombinant baculovirus at a multiplicity of infection of between 1:1 and 1:100 determined empirically. The supernatant is collected 7 days post infection. The pelleted cells are resuspended in 1% SDS and vortexed for 5 minutes to remove polyhedra. After three washes, the viral titer is determined. Approximately $1 \times 10^6$ recombinant plaque forming units are injected into larvae and the toxic effect of the virus encoding SEQ ID NO:3 (16 kDa toxin cDNA) is determined relative to wild-type baculovirus similarly treated. Oral infection is assayed by inoculating the larval diet with similar amounts of recombinant and wild-type baculovirus and observing their relative effects.

Example 15

Recombinant Baculovirus Containing SEQ ID NO:4 (30 kDa toxin cDNA): A recombinant baculovirus harboring the SEQ ID NO:4 (30 kDa toxin cDNA), or any modification thereof, is constructed by the method described in Example 14 employed for the SEQ ID NO:3 (16 kDa toxin cDNA).

Example 16

Recombinant Baculovirus containing multiple *Bracon venom* components. A recombinant baculovirus harboring the SEQ ID NO:3 (16 kDa toxin cDNA) and SEQ ID NO:4 (30 kDa toxin cDNA) is constructed by the method described in Example 14, except that the commercially available vector, p2Bac, obtained from Invitrogen, is used.

Example 17

Inhibition of Paralytic activity of a *Bracon venom* fraction by treatment with serine protease inhibitors. Pefabloc® SC (p-amino-ethylbenzenesulfonyl fluoride) is a water soluble, irreversible serine protease inhibitor which selectively inhibits trypsin- and chymotrypsin-like enzymes. Because some regions of the 30 kDa protein primary sequence (SEQ ID NO:2) were similar to known serine protease primary sequences, an inhibition experiment was carried out to determine whether protease activity was important for the paralyzing action of the toxin.

A sample of "Bracon toxin actives" (Table 1) was incubated with either buffer (50 mM sodium borate, 0.1M sodium chloride, pH 9.0) or 2 mg/ml Pefabloc® SC in the same buffer for four hours at 0° C. These solutions were then injected into *Heliothis virescens* (5 μl), and results were recorded 48 hours later. Five of 6 larvae injected with the control "Bracon toxin actives" were paralyzed, while the larvae injected with the Pefabloc® SC treated "Bracon toxin actives" were unaffected (8 out of 8). Larvae injected with Pefabloc® SC in buffer (no "Bracon toxin actives" in the sample) also were unaffected (6 out of 6). This strongly suggests that the enzymatic activity of the 30 kDa toxin is important for the paralytic effect of the Bracon venom.

Example 18

Mammalian system toxicity of Bracon venom fractions: Venom glands/reservoirs and associated structures were dissected from female *B. hebetor* wasps which had been killed by freezing at 70° C. A twenty-four (24) mg sample of this dissected tissue was suspended in 500 μl phosphate-buffered physiological saline, pH 6.5 (PBS), and disrupted by sonication. The resulting homogenate was spun at 13,000 rpm in a microcentrifuge for 10 minutes, and the supernatant was sterilized by 0.2μ microfiltration. All tissue homogenization, centrifugation, and filtration steps prior to the initiation of chromatography were carried out on ice or at a constant temperature of 4° C.

At a dose of 5 μl per larva, this extract irreversibly paralyzed tobacco budworm and beet armyworm larvae within 30 minutes of injection (n=3; all tested larvae were paralyzed, while control larvae were unaffected by injection of 5 μl PBS). The extract was then diluted 1:50 and tested in a rat hippocampal slice electrophysiology assay, which is capable of detecting a variety of effects on mammalian neurons. A 100 μl aliquot of the diluted extract has no effect in this assay. The remainder of the diluted extract was tested in TBW to confirm activity. Larvae were injected with 15 μl or 3 μl of the extract; controls were injected with 15 μl PBS. The 15 μl dose paralyzed 2 of 4 larvae within 24 hours, while the 3 μl dose caused feeding inhibition in 2 of 4 larvae within 24 hours. Controls were unaffected. Thus, an amount of material sufficient to paralyze about one dozen budworm larvae had no effect in the rat hippocampal brain slice assay.

In a second experiment, a 130 mg sample of dissected venom glands/reservoirs and associated tissues was suspended in 1 ml PBS, pH 6.5, and processed as described above. A 1:10 dilution of this extract, injected at a dose of 10 μl/larva, irreversibly paralyzed 2 of 4 TBW larvae within 24 hours. Two male Swiss-Webster mice (approximately 25 grams each) were given intracerebroventricular injections of the undiluted extract, at a dose of 5 μl per mouse. The mice appeared slightly sluggish for about 15 minutes after injection, although they responded normally to auditory stimuli. Within one hour after injection, the mice had resumed normal activity levels; no further effects were noted. Thus, i.c.v. administration of Bracon venom gland extract, in an amount sufficient to paralyze ≧10 TBW larvae, had no significant effects in mice.

In another series of tests for mammalian toxicity, highly purified venom fractions from *Bracon mellitor* were tested in TBW larvae and then tested for potential mammalian toxicity. These fractions were prepared by the following sequence. An extract of isolated female abdomens was fractionated by immobilized metal (copper) affinity chromatography, using methods analogous to those described elsewhere in this specification for fractionating *B. hebetor* extracts. Fraction 4 from this separation (C4), which contained most of the biological activity, was further fractionated by anion-exchange chromatography, using methods analogous to those described elsewhere in this specification for fractionating *B. hebetor* extracts. Fraction 4 from the anion-exchange separation (A4), which contained most of the biological activity, was further separated by hydrophobic interaction chromatography, as follows. Samples were loaded onto a Baker HI Propyl column (4.6×250 mm) in 50 mM monobasic sodium phosphate, pH 8.1, containing 1M NaCl. Elution buffer "A" was the loading buffer without the additional NaCl; elution buffer "B" was buffer "A" containing 2M NaCl; thus, the laoding buffer was a 1:1 mixture of "A" and "B". After the fractions were loaded, the proportion of "A" in the elution buffer was increased from 50% to 100% over 20 minutes. Fractions were collected on the basis of absorbance at 280 nm. Fractions 1 and 3 from this separation (C4/A4/HI and C4/A4/H3, respectively) were paralytic in TBW larvae when injected at 5 μl/larva after a 1:4 dilution in PBS. At 24 hr. after injection, fraction C4/A4/H1 had paralyzed 4 of 5 larvae, while fraction C4/A4/H3 had paralyzed 3 of 5 larvae; controls were unaffected.

Following this confirmation of insecticidal activity, the fractions were tested for mammalian toxicity. A 100 μl sample of each fraction (full strength, not the 1:4 dilution) was tested in the rat hippocampal slice electrophysiology assay; no effects were noted. Judging from the results of the 1:4 dilution assay in TBW, 100 μl of the stock should have been enough to paralyze 50 to 60 TBW larvae. This suggests that the active components of these *B. mellitor* fractions have a high degree of selectivity for insects. Fraction C4/A4/H1 was also tested in whole cell voltage-clamped cardiac myocytes. 50 μl of the undiluted stock (as tested in the hippocampal assay) was put into the myocyte assay (total volume 5 ml). This dose was sufficient to paralyze about 30 TBW larvae, but there was no effect on the myocytes. Again, this suggests that Bracon insecticidal toxins have a high degree of selectivity for insects.

SUMMARY

The present invention relates to insecticidally effective toxins isolated from the wasp, *Bracon hebetor* and other species in the genus Bracon, characterized by their neurotoxic effect on insect pests. When small, insecticidally effective, quantities of venom fractions containing these toxins are administered to selected insects, the insects are paralysed or killed.

As described above, the present invention also relates to the cloning of these toxins using routine recombinant DNA technology. The amino acid sequence of one of these toxins, SEQ ID NO:2 (30 kDa toxin), has homology to known serine proteases.

The present invention also provides methods for modifying and improving the described toxins for use as insecticidal agents. In addition, the present invention relates to the use of these toxins as agents for combating insect pests. Large quantities of these toxins may be obtained using known recombinant technology methods. The toxins can be engineered into an expression vector which is then inserted into either a prokaryotic host, such as *E. coli*, or a eukaryotic host, such as insect cells. The isolated protein may then be applied directly to the plant or animal sought to be protected from insect pests.

As an alternative, as described above, the toxins may be engineered into a natural pathogen of insects such as Bacillus or baculovirus. The recombinant pathogens can be utilized to transfer the peptides directly into the insect pests. These recombinantly engineered pathogens will have significantly increased toxicity.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fraction of whole Bracon wasp venom which is characterized by its neurotoxic effect on *Heliothis virescens* comprising SEQ ID NO:2 (30 kDa toxin).

2. A substantially purified, insecticidally effective peptide isolated from Bracon wasp venom characterized by its neuorotoxic effect on insect pests, said peptide comprising SEQ ID NO:2.

3. An insect toxin comprising the amino acid sequence of SEQ ID NO:2 (30 kDa toxin) or a functional derivative or fragment thereof which is toxic to insects.

4. A nucleic acid sequence comprising nucleotides which code for the amino acid sequence of SEQ ID NO:2 (30 kDa toxin) or a functional derivative or fragment thereof.

5. A nucleic acid sequence as defined in claim 4 wherein the nucleic acid sequence is subcloned into a plasmid.

6. A nucleic acid sequence as defined in claim 4 wherein the nucleic acid sequence is subcloned into a prokaryotic, eukaryotic or baculovirus expression vector.

7. A nucleic acid sequence as defined in claim 4 wherein the nucleic acid sequence is stably or transiently incorporated into a prokaryotic or eukaryotic host.

8. A nucleic acid sequence as defined in claim 4 wherein the nucleic acid sequence is stably or transiently incorporated into a baculovirus host.

9. A host cell comprising the nucleic acid sequence of claim 4.

10. The host cell of claim 9, wherein the host cell is a eukaryotic host cell.

11. The host cell of claim 9, wherein the host cell is a prokaryotic host cell.

12. A method of controlling insects comprising exposing insects to an insecticidally effective quantity of a peptide comprising the amino acid sequence of SEQ ID NO:2 (30 kDa toxin) or a functional derivative or fragment thereof which is toxic to insects.

13. A method of controlling insect pests comprising exposing insects to a recombinant baculovirus host containing a nucleic acid sequence which codes for the amino acid sequence of SEQ ID NO:2 (30 kDa toxin) or any functional derivative or fragment thereof which is toxic to insects.

* * * * *

UNITED STATES PATENT AND TRADEMARK OFFICE
CERTIFICATE OF CORRECTION

PATENT NO. : 5,874,298
DATED : February 23, 1999
INVENTOR(S) : Johnson et al.

It is certified that error appears in the above-identified patent and that said Letters Patent is hereby corrected as shown below:

On the title page, please amend the title to read --30kD Insecticidal Toxins from *Bracon Hebetor* Nucleic Acid Encoding Said Toxin and Methods Of Use--.

In column 1, line 1, before "Insecticidal", please insert -- 30kD --.

In column 33, sequence no. 7, section (ix) (D), please delete "Xaa a tyrosine or proline" and insert --Xaa at location 6 is either lysine or alanine, Xaa at location 8 is either cysteine or asparagine, Xaa at location 12 is either alanine or cysteine, and Xaa at location 18 is either tyrosine or proline.--

In column 33, sequence no. 9, section (ix) (D), after "N at p", please insert --osition 19 is M--.

Signed and Sealed this

Fourteenth Day of December, 1999

Attest:

Q. TODD DICKINSON

Attesting Officer

Acting Commissioner of Patents and Trademarks